Figure 1:
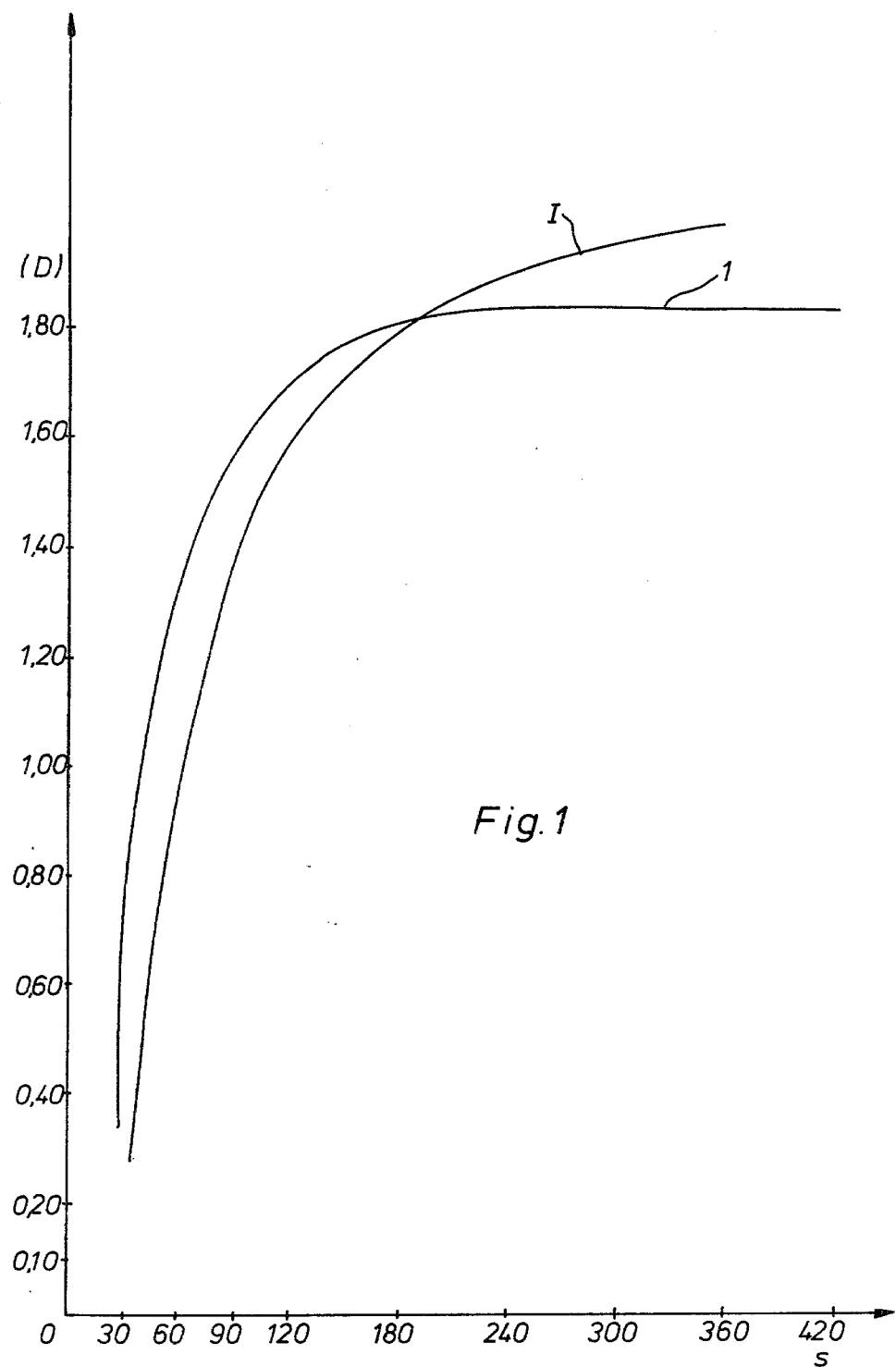
Figure 2:
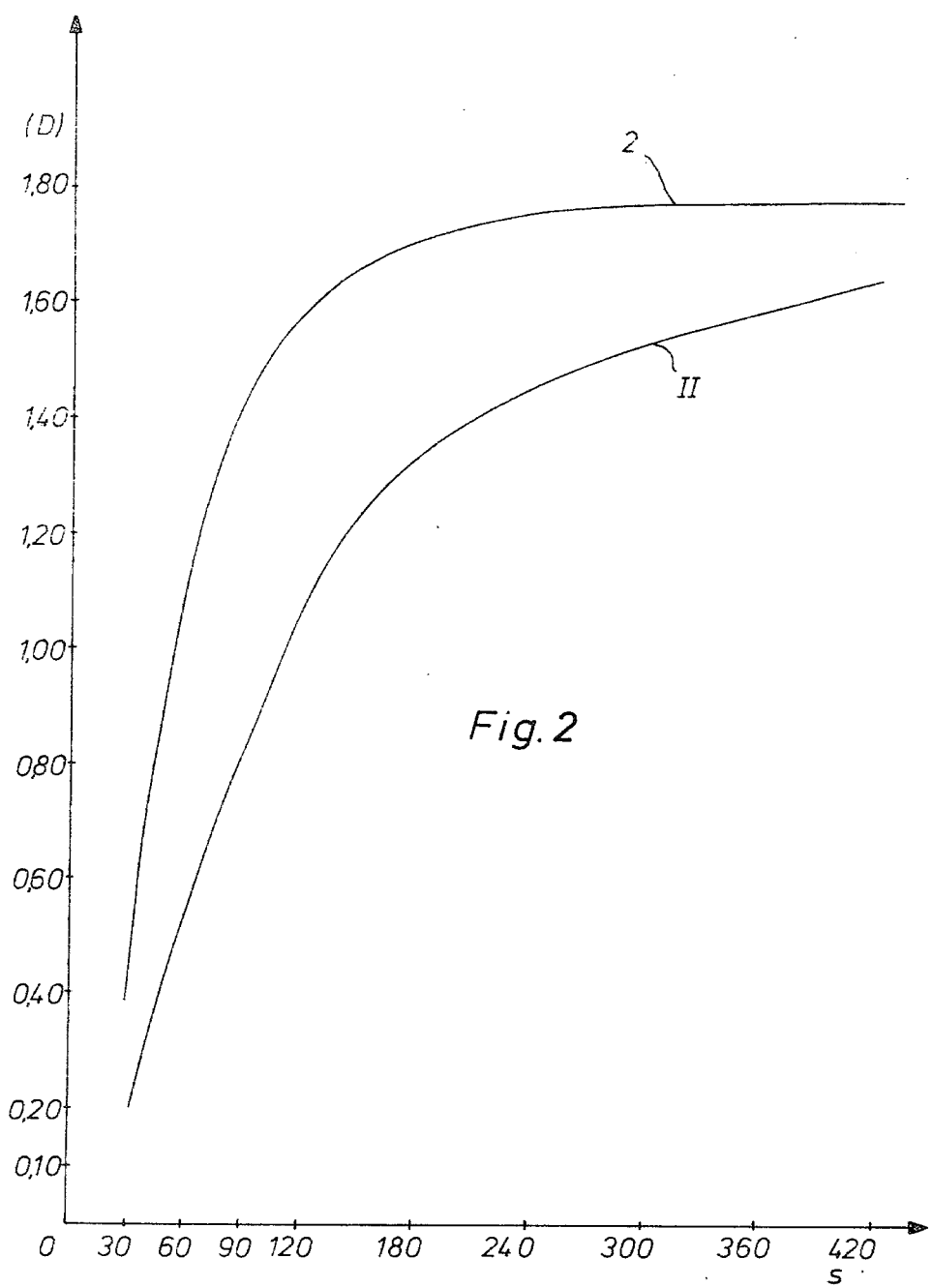
Figure 3:
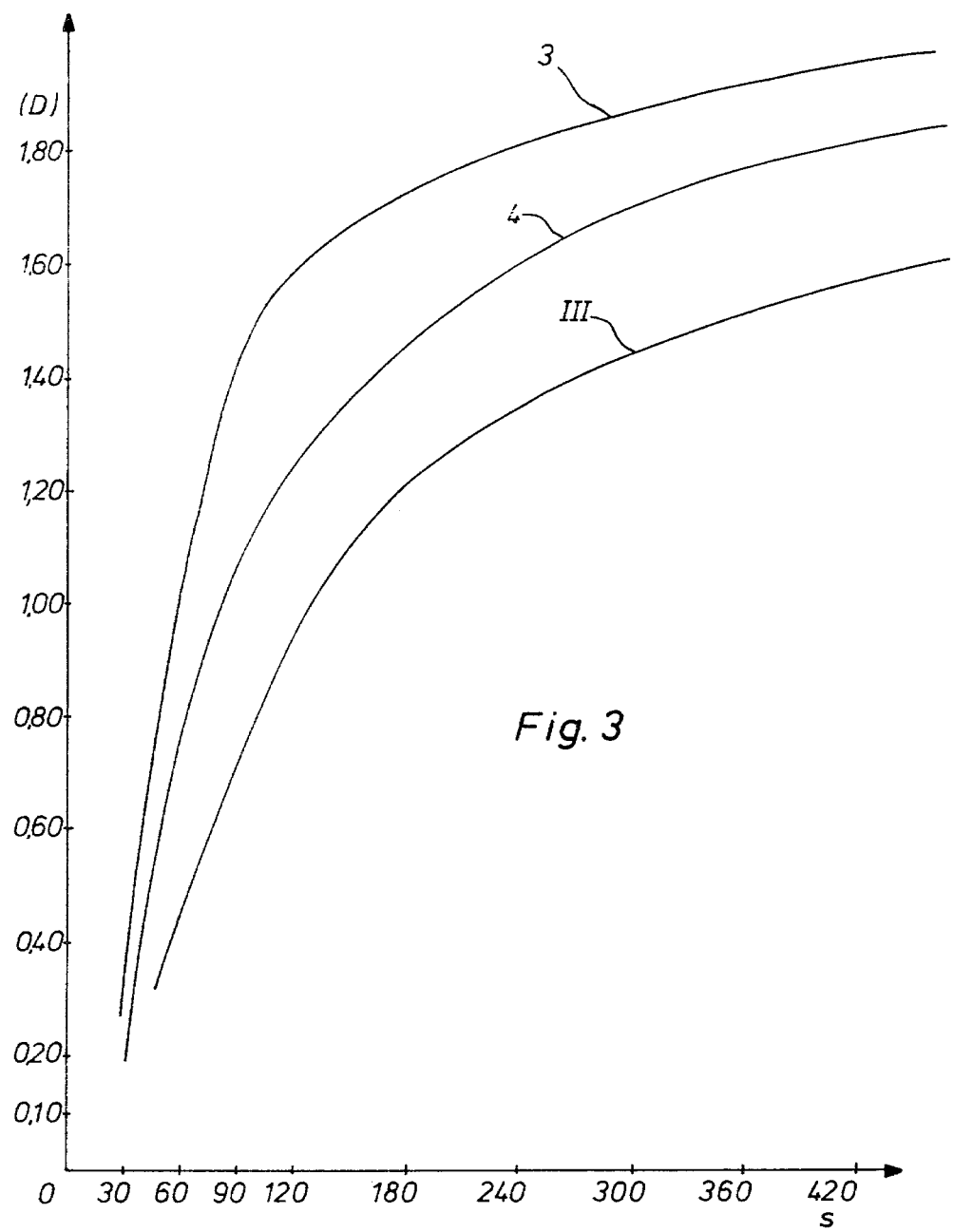

United States Patent [19]

Jaeken et al.

[11] 4,273,855
[45] Jun. 16, 1981

[54] PHOTOGRAPHIC DIFFUSION TRANSFER PROCESS AND MATERIAL FOR THE PRODUCTION OF COLOR IMAGES AND SUITABLE COMPOUNDS THEREFOR

[75] Inventors: Jan Jaeken, Hove; André Verhecken, Mortsel, both of Belgium; Hans Vetter, Cologne; Paul Marx, Leverkusen, both of Fed. Rep. of Germany

[73] Assignee: Agfa-Gevaert N.V., Mortsel, Belgium

[21] Appl. No.: 19,582

[22] Filed: Mar. 12, 1979

[30] Foreign Application Priority Data

Mar. 17, 1978 [DE] Fed. Rep. of Germany ....... 2811720

[51] Int. Cl.³ .......... G03C 1/40; G03C 1/10; G03C 7/00; G03C 5/54
[52] U.S. Cl. .................. 430/242; 430/223; 430/559
[58] Field of Search ......... 96/29 D, 77, 99, 100, 96/52, 56.2, 56.6, 54; 430/223, 242, 561, 559

[56] References Cited

U.S. PATENT DOCUMENTS 4,156,608  5/1979  Vetter et al. .................. 96/77

OTHER PUBLICATIONS

*Research Disclosure* No. 15654 4/1977.

*Primary Examiner*—Richard L. Schilling
*Attorney, Agent, or Firm*—A. W. Breiner

[57] ABSTRACT

A compound of the following formula and use of this compound in a photographic material and a photographic diffusion transfer process for the production of color images:

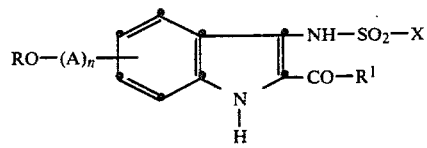

wherein
R represents a hydrogen atom or an alkyl group with 1 to 4 C atoms;
A represents an oxyalkylene group, such as —CH$_2$—CH$_2$—O—;
n represents 1 or 2;
X represents a residue of a dye or a dye precursor, which either directly or by means of an intermediate link Z is linked to the SO$_2$-group;
Z represents an alkylene group of 1 to 6 C atoms, an arylene group, or a heterocyclic group, which is linked to the residue X either directly or by means of —O—, —S—, —SO$_2$—, —NR— (R being hydrogen or an alkyl group), —CO—, —CO—NH—, or —SO$_2$—NH—;
R$^1$ represents —OR$^2$, —SR$^2$ or

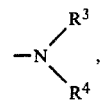

R$^2$ being hydrogen, an alkyl group with 1 to 22 C atoms, a cycloalkyl group or an aryl group wherein said alkyl, cycloalkyl and aryl groups may be further substituted, R$^3$ being one of the residues defined under R$^2$ or being an acyl residue, which is derived from an aliphatic or aromatic carboxylic or sulphonic acid, and R$^4$ being hydrogen or optionally a substituted alkyl group with 1 to 22 C atoms.

3 Claims, 4 Drawing Figures

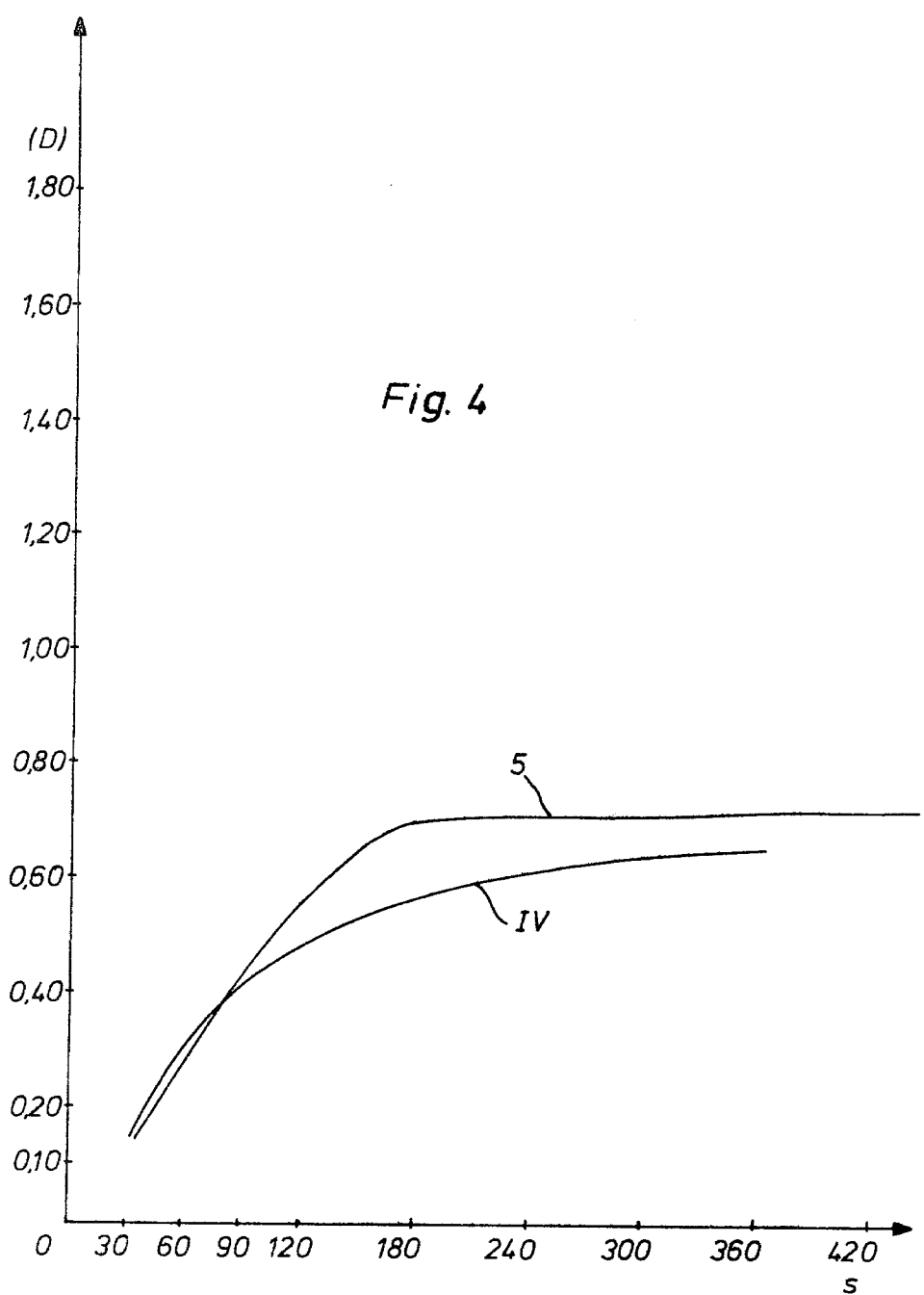

PHOTOGRAPHIC DIFFUSION TRANSFER PROCESS AND MATERIAL FOR THE PRODUCTION OF COLOR IMAGES AND SUITABLE COMPOUNDS THEREFOR

This invention relates to a photographic diffusion transfer process and a material for the production of colour images and suitable compounds therefor.

The object of the published German Patent Application No. 2,645,656 filed Oct. 9, 1976 by Agfa-Gevaert AG is a photographic dye diffusion transfer process for making colour images, according to which a photographic material comprising at least one light-sensitive silver halide emulsion layer and a non-diffusing colour-providing compound associated therewith, which in its oxidized form in the alkaline developer medium is capable of releasing a diffusable dye, is exposed image-wise and developed with a developing agent for silver halide, wherein the latter in its oxidized form oxidizes the non-diffusing colour-providing compound, which is split by the developer alkali as a result of this oxidation under the formation of an image-wise distribution of released diffusing dye, characterized in that the non-diffusing colour-providing compound corresponds to the following general formula:

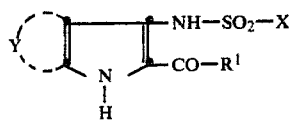

wherein:
X represents the residue of a dye or dye precursor, which either directly or by means of an intermediate link Z is bound to the SO$_2$-group;
Z represents an alkylene group with 1 to 6 C atoms, an arylene group or a heterocyclic group, which either directly or indirectly through —O—, —S—, —SO$_2$—, —NR— (R being hydrogen or an alkyl group), —CO—, —CO—NH— or —SO$_2$—NH— is linked to the residue X;
Y represents the residue necessary for completing an anellated benzene ring, which optionally is simply or multiply substituted;
R$^1$ represents —OR$^2$, —SR$^2$ or

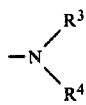

R$^2$ being hydrogen, an alkyl group with 1 to 22 C atoms such as methyl, ethyl, isopropyl, n-octadecyl, cycloalkyl such as cyclohexyl, or an aryl group such as phenyl; the said alkyl, cycloalkyl and aryl groups may be further substituted, e.g. the alkyl group by hydroxyl, alkoxy, aryloxy, halogen, carboxyl or sulpho, and the aryl group by halogen, alkyl, alkoxy, dialkylamino, acylamino, carboxyl or sulpho, R$^3$ being one of the residues defined under R$^2$ or being an acyl residue which is derived from an aliphatic or aromatic carboxylic or sulphonic acid, and R$^4$ being hydrogen or an optionally substituted alkyl group with 1 to 22 C atoms.

It is an object of the present invention to provide new, non-diffusing colour-providing compounds for said photographic diffusion transfer process and material, which compounds combine a higher reactivity with the required stability and which offer a higher dye transfer with a higher sensitivity, keeping fog as low as possible.

The non-diffusing colour-providing compounds of the present invention correspond to the following general formula:

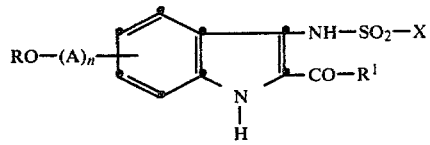

wherein
R represents hydrogen or an alkyl group with 1 to 4 C atoms such as methyl, ethyl, isopropyl and butyl;
A represents an oxyalkylene group such as —CH$_2$—CH$_2$—O—;
n is 1 or 2;
X represents the residue of a dye or dye precursor, which is linked to the —SO$_2$-group either directly or indirectly through an intermediate group Z;
Z represents an intermediate group such as an alkylene group with 1 to 6 C atoms, an arylene group or a heterocyclic group, which are bound to the residue X either directly or indirectly through —O—, —S—, —SO$_2$—, —NR— (R being hydrogen or an alkyl group), —CO—, —CONH— or —SO$_2$NH—; and
R$^1$ represents —OR$^2$, —SR$^2$ or

R$^2$ being hydrogen, an alkyl group with 1 to 22 C atoms such as methyl, ethyl, isopropyl, n-octadecyl, cycloalkyl such as cyclohexyl, or an aryl group such as phenyl; said alkyl, cycloalkyl and aryl groups may be further substituted, e.g. the alkyl group by hydroxyl, alkoxy, aryloxy, halogen, carboxyl or sulpho, and the aryl group by halogen, alkyl, alkoxy, dialkylamino, acylamino, carboxyl or sulpho, R$^3$ being one of the residues defined under R$^2$ or being an acyl residue which is derived from an aliphatic or aromatic carboxylic or sulphonic acid, and R$^4$ being hydrogen or an optionally substituted alkyl group with 1 to 22 C atoms.

By operating the photographic diffusion transfer process for the production of colour images by means of the above mentioned colour-providing compounds of the invention in a two-sheet system the light-sensitive material and the image-receiving material are to be held in contact only for a short time to achieve already a high colour density in the receiving material and such with the further advantage that the colour density hardly changes after a relatively long period of contact; in other words independently of the time of contact a constantly reproducible image quality is obtained very rapidly.

It has to be pointed out that the colour-providing compounds according to the invention should not diffuse in the layers of the photographic material in the form of intact molecules. For that purpose they contain a residue making the molecule non-migratory, e.g. in the residue $R^1$. A sufficient fastness to diffusion of the colour-providing compounds can already be realized if $R^1$ does not contain a relatively long alkyl chain, since even then the molecule, depending on the dye residue, may be sufficiently large. Otherwise, the colour-providing compounds can be made sufficiently non-migratory by choosing residues of suitable length.

Those residues making non-migratory make it possible to incorporate in a non-migratory way the compounds according to the invention into the hydrophilic colloids that are normally used in photographic materials. For that purpose preferably organic residues are suited, which generally contain straight or branched aliphatic groups and optionally also isocyclic or heterocyclic or aromatic groups generally comprising 8 to 20 C atoms. These residues are linked to the rest of the molecule either directly or indirectly, e.g. through one of the following groups: —NHCO—, —NHSO$_2$—, —NR— (R being hydrogen or alkyl), —O—, —S— or —SO$_2$—. In addition thereto the residue making non-migratory can also contain water-solubilizing groups, e.g. sulpho groups or carboxylic groups, which may be present in anionic form. As the properties of diffusion depend on the molecular size of the used compound as a whole, it is sufficient in some cases, e.g. if the overall structure of the molecule is sufficiently large, to use also shorter-chain residues as residues making fast to diffusion. In principle the residues of dyes of all dye classes are suited as far as they are sufficiently diffusable for passing through the layers of the light-sensitive material into the image-receiving layer. For that purpose the dye residues may be provided with one or more water-solubilizing groups. Examples of suitable water-solubilizing groups are carboxyl groups, sulpho groups, sulphonamide groups as well as aliphatic or aromatic hydroxyl groups.

However, the sulphonamide group remaining in the dye molecule after cleavage of the oxidized colour-providing compound confers to the dye molecule already a considerable tendency to diffusion in alkaline medium so that the presence of additional water-solubilizing groups is not absolutely necessary. Examples of particularly suitable dyes for the process of the present invention are: azo dyes, azomethine dyes, anthraquinone dyes, phthalocyanine dyes, indigoid dyes, triphenylmethane dyes as well as metall complex dyes or coloured metall complexes.

Under the residues of dye precursors the residues of those compounds have to be understood that in the course of photographic processing are transformed into dyes by usual or additional processing steps either by oxidation or by coupling or uncovering of an auxochromic group in a chromophoric system, e.g. by saponification. Dye precursors in this sense may be leuco dyes, colour couplers or also dyes that are transformed into other dyes during processing. As far as a distinction between dye residues and residues of dye precursors is of no essential importance, the latter are also to be understood under the term dye residues in the following description. Examples of suitable colour-providing compounds according to the present invention are listed in table 1.

TABLE 1

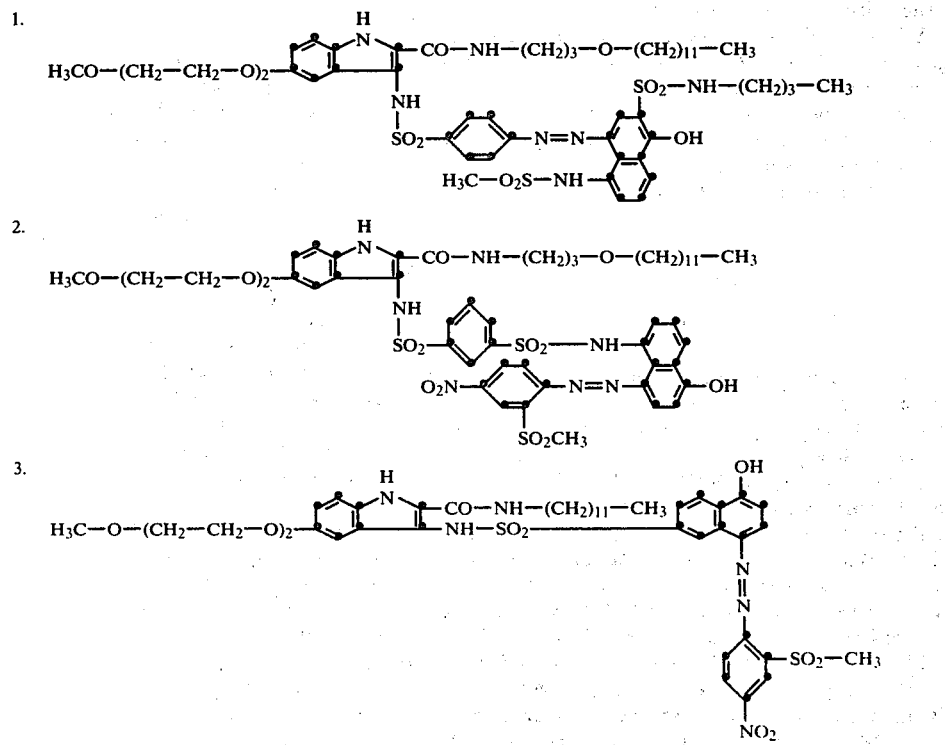

TABLE 1-continued

4.
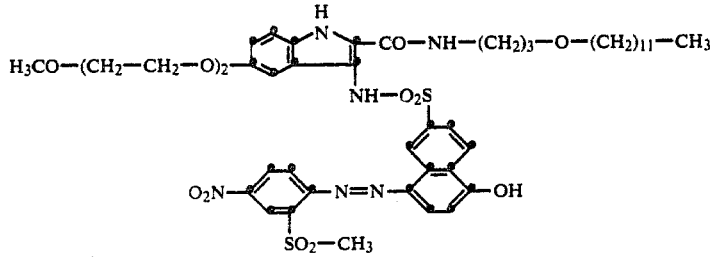

5.
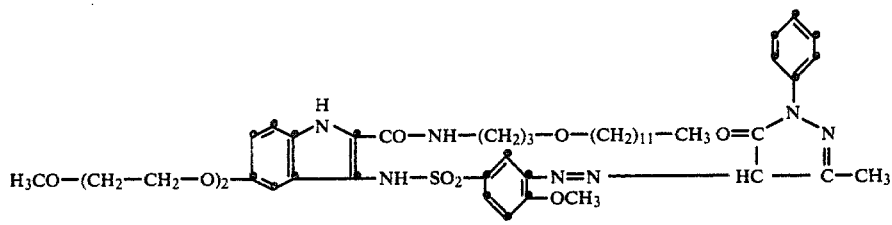

6.
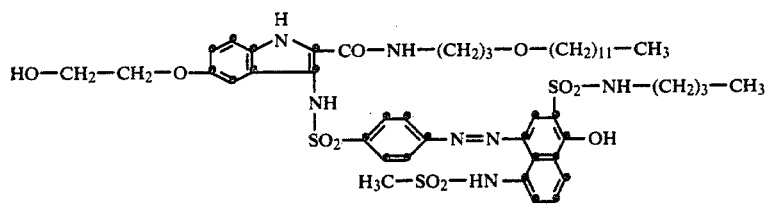

7.
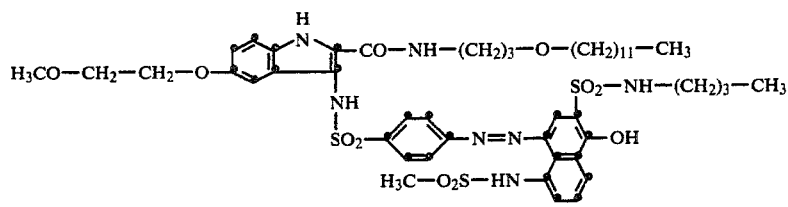

8.
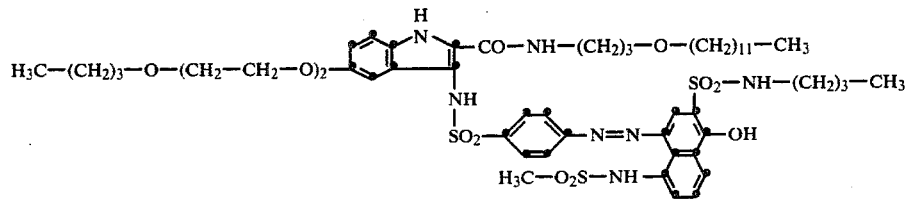

The compounds 1, 6, 7 and 8 are magenta dye-providing compounds, the compounds 2, 3 and 4 are cyan dye-providing compounds and the compound 5 is a yellow dye-providing compound.

The preparation of the colour-providing compounds 1 to 8 is exemplified hereinafter.

Colour-providing compound 1

52 g of 5-[β-(β'-methoxyethoxy)-ethoxy]-3-amino-2-[N-(γ-lauryloxypropyl)-carbonamido]-indole and 6 g of ascorbic acid are dissolved at 40° C. in 700 ml of ethylene glycol monomethyl ether. Then a solution of 28 ml of triethylamine in 50 ml of ethylene glycol is added dropwise while 74.5 g of 5-methylsulphonamido-4-(p-chlorosulphonylphenylazo)-1-hydroxy-2-N-butylnaphthalinesulphonamide are added portionwise. The mixture obtained is diluted with 300 ml of water, acidified with 70 ml of strong hydrochloric acid and stirred, until the formed precipitate becomes granular. The precipitate is filtered with suction, stirred in a mixture of ethanol and water (4/1), filtered with suction, washed with diluted ethanol and recrystallized from acetonitrile.

Yield: 78 g. Melting point: about 160° C.

Thin-layer chromatography with methylene chloride/methanol (80/20) mixture as an eluent gives a very faint side-spot.

Starting product 1.1

4-[β-(β'-methoxyethoxy)-ethoxy]-nitrobenzene

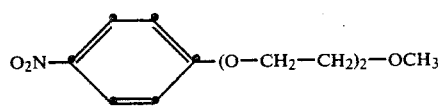

1224 g of p-nitroanisol, 3840 ml of diethylene glycol monomethyl ether and 132 g of potassium hydroxide are heated at 90° C. for 2.5 h under the reduced pressure produced with a water-jet pump. Thereupon 2 l of ice-water are added, and the solid product is filtered with suction, washed with 4 l of a mixture of ethanol and water (50% by volume) and dried.

Yield: 1750 g of the above starting product. Melting point: 79° C.

Starting product 1.2

4-[β-(β'-methoxyethoxy)-ethoxy]-aniline

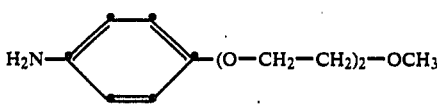

1.446 kg of 4-[β-(β'-methoxyethoxy)-ethoxy]-nitrobenzene are dissolved in 1.6 l of anhydrous ethanol and hydrogenated in the presence of Raney nickel under a hydrogen pressure of 10,500 kPa at 60° C.

After filtration of the catalyst the solvent is eliminated in a rotary evaporator, whereupon the residue is distilled under reduced pressure.

Boiling point: 150° C. at 40 Pa (0.3 mm of Hg).
Yield: 96%.

Intermediate product 1.1

5-methylsulphonamido-4-(p-chlorosulphonyl-phenylazo)-1-hydroxy-2-N-butylnaphthaline sulphonamide

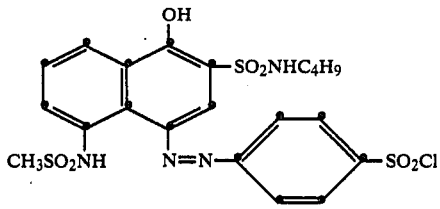

A mixture of 250 g of sodium salt of 5-methylsulphonamido-4-(p-sulphophenylazo)-1-hydroxy-2-N-butylnaphthaline sulphonamide, 1250 ml of phosphorus oxychloride and 53 ml of N-methylpyrrolidone is heated at 60° C. with stirring for 6 h and then cooled. The precipitate formed is filtered with suction, washed with dichloroethane and dried.

Yield: 182 g. Melting point: above 260° C.

By thin-layer chromatography with methylene chloride/methanol mixture (95/5) as an eluent only a faint side-spot is detected.

Intermediate product 1.2

Sodium salt of 5-methylsulphonamido-4-(p-sulphophenylazo)-1-hydroxy-2-N-butylnaphthaline sulphonamide

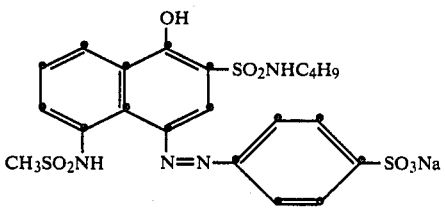

A solution of 52.6 g of sodium nitrite in 124 ml of water is added at 10° C. to a solution of 116 g of sulphanilic acid in 2060 ml of water. The solution obtained is slowly added with stirring to a mixture of 143 ml of strong hydrochloric acid and 800 g of ice. After stirring for 15 min the excess nitrite possibly left is destroyed with 18 g of urea.

The diazonium solution obtained is slowly added at 5° to 10° C. to a solution of 165 g of 5-methylsulphonamido-1-hydroxy-2-N-butylnaphthaline sulphonamide and 125 g of sodium hydroxide in 2130 ml of water whereupon stirring is continued for 1 h. Thereafter first 300 ml of acetic acid and then 600 g of sodium chloride are added to the mixture. The precipitate formed is filtered with suction, washed with 10% sodium chloride solution and dried.

Yield: 250 g.

By thin-layer chromatography with an ethyl acetate/methanol/ammonium hydroxide solution (60/20/20) as an eluent four very faint side-spots are detected.

Intermediate product 1.3

5-methylsulphonylamino-1-hydroxy-2-N-butylnaphthaline sulphonamide

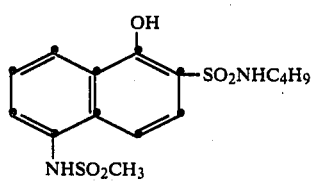

A mixture of 275 g of 5-bis(methylsulphonyl)-amino-1-hydroxy-2-N-butylnaphthaline sulphonamide, 639 ml of 45% aqueous potassium hydroxide solution and 2500 ml of ethanol is stirred for 3 h at room temperature, poured in 10 l of water and acidified with strong hydrochloric acid. Then an excess of 375 ml of hydrochloric acid is added, whereupon the precipitate obtained is filtered with suction, washed with water, recrystallized from dichloroethane and washed with n-hexane.

Yield: 165 g. Melting point: 163° C.

By thin-layer chromatography with a methylene chloride/methanol mixture (95/5) as an eluent only at the beginning a faint side-spot is detected.

Intermediate product 1.4

5-bis(methylsulphonyl)-amino-1-hydroxy-2-N-butyl-naphthaline sulphonamide

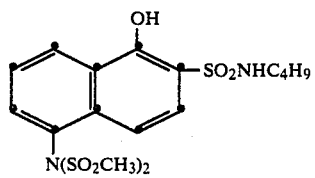

A mixture of 385 g of 5-bis(methylsulphonyl)-amino-1-methylsulphonyloxy-2-naphthaline sulphonyl chloride (prepared according to the published Dutch Patent Application No. 75/01348 filed Feb. 5, 1975 by Eastman Kodak Company), 202 ml of butylamine, 17.6 ml of diisopropylethylamine and 4720 ml of dioxan is stirred with reflux for 2 h. Then active carbon is added to the mixture whereupon the whole is filtered while hot. The filtrate is poured into water with stirring, whereafter the precipitate formed is filtered with suction, again stirred under water, filtered with suction and dried.

Yield: 275 g. Melting point: 152 g.

By thin-layer chromatography with a methylene chloride/methanol mixture (98/2) only two faint side-spots are obtained.

Intermediate product 1.5

5-[β-(β'-methoxyethoxy)-ethoxy]-3-amino-2-[N-(γ-lauryloxypropyl)-carbonamido]-indole

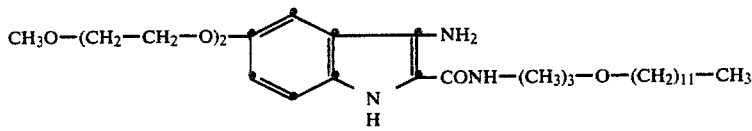

515 g of 5-[β-(β'-methoxyethoxy)-ethoxy]-3-(p-methoxyphenylazo)-2-[N-(γ-lauryloxypropyl)-carbonamido]-indole, mixed with 1930 ml of ethyl acetate, are reduced with Raney nickel as a catalyst at 70° C. under a hydrogen pressure of $10^4$ kPa. The catalyst is filtered off and the filtrate is concentrated in a rotary evaporator to an amount of 1250 ml. Then 2500 ml of benzine are added whereupon the precipitate formed is filtered with suction, washed with 500 ml of benzine and dried.

Yield: 380 g. Melting point: 81° C.

By thin-layer chromatography with a methylene chloride/methanol mixture (90/10) as an eluent still two very faint side-spots are obtained.

Intermediate product 1.6

5-[β-(β'-methoxyethoxy)-ethoxy]-3-(p-methoxyphenylazo)-2-[N-(γ-lauryloxypropyl)-carbonamido]-indole

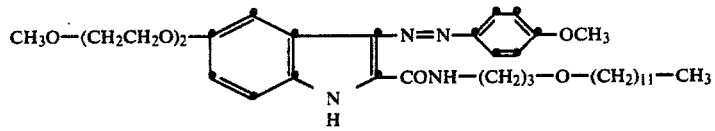

135 g of p-anisidine, mixed with 275 g of ice and 275 ml of strong hydrochloric acid, are diazotized at 0° C. with a solution of 80 g of sodium nitrite in 200 ml of water. The mixture is stirred for a further 30 min and the excess nitrite is destroyed with a little urea.

To a solution of 504 g of 5-[β-(β'-methoxyethoxy)ethoxy]-2-[N-(γ-lauryloxypropyl)-carbonamido]-indole in 2 l of dimethylformamide first 8 l of ethylene glycol monomethyl ether and then 132 g of potassium hydroxide are added. The diazonium solution is gradually added to the solution obtained. The new mixture is stirred for still 1 h, whereupon 63 ml of acetic acid are added, the precipitate formed is filtered with suction, washed with 1000 ml of methanol, stirred in 5 l of water, filtered with suction, washed with 1500 ml of methanol and dried.

Yield: 510 g. Melting point: 102° C.

By thin-layer chromatography with a methylene chloride/methanol mixture (95/5) as an eluent still three faint side-spots are detected.

Titration with sodium ethylate in dimethylformamide gives 1.53 meq/g. Calculated value: 1.567 meq/g.

Intermediate product 1.7

5-[β-(β'-methoxyethoxy)-ethoxy]-2-[N-(γ-lauryloxypropyl)carbonamido]-indole

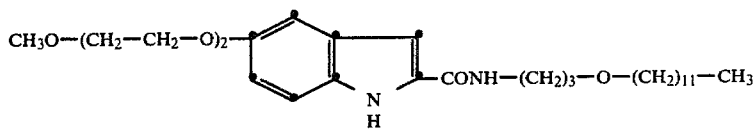

A mixture of 461 g of 5-[β-(β'-methoxyethoxy)-ethoxy]-2-carbethoxy-indole, 401 g of γ-lauryloxypropylamine and 1950 ml of toluene is made anhydrous by distilling 150 ml of toluene. The mixture is allowed to cool to 100° C. whereupon a solution of 6.9 g of sodium in 120 ml of methanol is added dropwise. The toluene is distilled and the mixture is allowed to cool to 60° C. Then 3 l of benzine and 18 ml of acetic acid are added successively whereupon the mixture is allowed to cool overnight in the refrigerator. The precipitate formed is filtered with suction, washed with benzine and dried.

Yield: 642 g. Melting point: 68° C.

By thin-layer chromatography with methylene chloride/methanol mixture (95/5) as an eluent two very faint side-spots are detected.

Titration with sodium methylate in dimethylformamide gives 1.99 meq/g. Calculated value: 1.984 meq/g.

Intermediate product 1.8

5-[β-(β'-methoxyethoxy)-ethoxy]-2-carbethoxy-indole

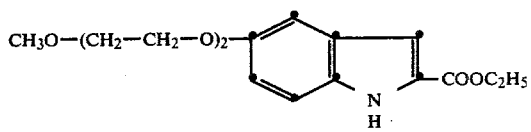

1185 g of crude 2-methyl-2-{4-[β-(β'-methoxyethoxy)-ethoxy]-phenylazo}-acetylacetic acid ethyl ester are added dropwise to 2 l of 3 N solution of hydrochloric acid in ethanol and refluxed for 1 h. Then 6 l of water are added and the obtained solution is extracted with a mixture of 2 l of toluene and 2.5 l of methylene chloride. The extract is washed trice with water, concentrated to a volume of about 1 l and cooled overnight in the refrigerator. The precipitate formed is filtered with suction, washed with a mixture of toluene and benzine and dried.

Yield: 450 g. Melting point: 92° C.

By thin-layer chromatography with methylene chloride/methanol mixture (95/5) as an eluent two faint side-spots are detected.

Titration with sodium methylate in dimethylformamide gives 3.24 meq/g. Calculated value: 3.257 meq/g.

Intermediate product 1.9

2-methyl-2-{4-[β-(β'-methoxyethoxy)-ethoxy]-phenylazo}-acetylacetic acid ethyl ester

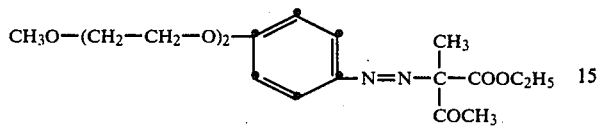

633 g of 4-[β-(β'-methoxyethoxy)-ethoxy]-aniline, mixed with 1240 g of ice and 820 ml of concentrated hydrochloric acid, are diazotized by adding dropwise a solution of 217 g of sodium nitrite in 600 ml of water at 0° C. The reaction mixture is stirred for another 30 min. Then the excess nitrite is destroyed by adding a solution of 20 g of urea in 20 ml of water. Just before the azo coupling the pH of the diazonium solution is adjusted to 5 by adding some sodium acetate. The solution is added at 0° C. to a solution of 563 g acetylacetic acid ethyl ester in 1240 ml of pyridine, stirred at 0° C. for 3 h and extracted with methylene chloride. The extract is washed successively with water, 5% hydrochloric acid and water, and evaporated in a rotary evaporator, whereupon the residual 1185 g of crude oily product are further transformed without purification.

By thin-layer chromatography with methylene chloride/methanol mixture (98/2) as an eluent two side-spots and two main spots are obtained, viz. one of the azo ester and one of the hydrazone. Both compounds are cyclized to indole according to the following step of synthesis.

Colour-providing compound 2

A mixture of 23.4 g of 5-[β-(β'-methoxyethoxy]-3-amino-2-[N-(γ-lauryloxypropyl)-carbonamido]-indole (intermediate product 1.5) 3 g of ascorbic acid and 450 ml of ethylene glycol monomethyl ether are stirred and heated to 60° C. Then 35.4 g of 3-[5-hydroxy-8-(2-methylsulphonyl-4-nitrophenylazo)-naphthylsulphamoyl]-benzene sulphochloride as well as a solution of 7.5 ml of triethylamine in 30 ml of ethylene glycol monomethyl ether are added portionwise and simultaneously. The mixture is diluted with 150 ml of water and acidified with 25 ml of strong hydrochloric acid. The precipitate formed is filtered with suction and washed with diluted ethanol. In order to eliminate the sulphonic acid optionally still present, the mixture is dissolved twice in ethylene glycol monomethyl ether and a little ascorbic acid and again precipitated with water.

Yield: 23.2 g.

By thin-layer chromatography with a methylene chloride/methanol mixture (80/20) as an eluent only a small amount of dye sulphonic acid is detected.

Intermediate product 2.1

3-[5-hydroxy-8-(2-methylsulphonyl-4-nitrophenylazo)-naphthylsulphamoyl]-benzene sulphochloride

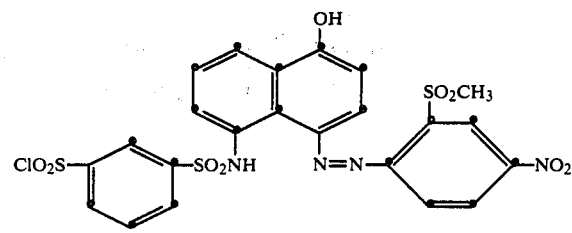

126 g of the sodium salt of 3-[5-hydroxy-8-(2-methylsulphonyl-4-nitrophenylazo)-naphthylsulphamoyl]-benzene sulphonic acid are stirred in 700 ml of phosphorus oxychloride and heated to 60° C. At this temperature 20 g of N-methylpyrrolidone are gradually added, whereupon the mixture is stirred at 60° C. for 6 h and thereafter allowed to cool. The precipitate formed is filtered with suction, washed with dichloroethane and dried.

Yield: 108 g. Melting point: above 260° C.

By thin-layer chromatography with a methylene chloride/methanol mixture (98/2) as an eluent a faint side-spot besides a small amount of dye sulphonic acid are detected. The product is used in the following step without any further purification.

Intermediate product 2.2

Sodium salt of 3-[5-hydroxy-8-(2-methylsulphonyl-4-nitrophenylazo)-naphthylsulphamoyl]-benzenesulphonic acid

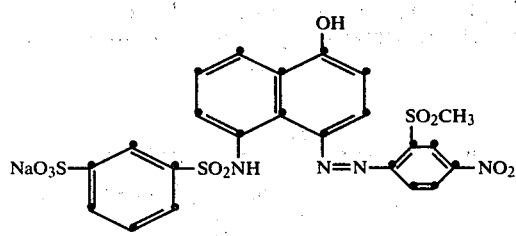

115 g of 3-[5-hydroxy-8-(2-methylsulphonyl-4-nitrophenylazo)-naphthylsulphamoyl]-benzene sulphonylfluoride (prepared according to the published German Patent Application No. 2,402,900 filed Jan. 22, 1974 by Eastman Kodak Company, page 60) are stirred in 2300 ml of water, whereupon 19 g of sodium hydroxide are added and the whole is gradually heated to 50° C. Then 6 g of sodium hydroxide are added to the mixture, which is stirred at 50° C. for another 30 min. Then 70 ml of strong hydrochloric acid are added, whereupon the mixture is cooled and salted out with sodium chloride. The precipitate formed is filtered with suction, washed with water and dried.

Yield: 148 g.

By thin-layer chromatography with a methylene chloride/ammonium hydroxide/methanol mixture (80/3/17) as an eluent still three very faint side-spots are obtained.

Colour-providing compound 3

11.5 g of 5-[β-(β'-methoxyethoxy)-ethoxy]-3-amino-2-N-laurylcarbonamido-indole are dissolved at 50° C. in 190 ml of ethylene glycol monomethyl ether. To this solution are gradually added 11.8 g of 5-hydroxy-8-(2-methylsulphonyl-4-nitrophenylazo)-2-naphthaline sulphonyl chloride (prepared according to the Belgian Patent Specification No. 796,041 filed Feb. 27, 1973 by Eastman Kodak Company, page 26) together with a solution of 5 ml of triethylamine in 10 ml of ethylene glycol monomethyl ether. The mixture is stirred at 50° C. for another hour and then allowed to cool. Then 100 ml of water are added and the mixture is acidified with hydrochloric acid. The precipitate formed is filtered with suction, washed with diluted methanol and dried.

Yield: 21.6 g.

By boiling first in acetonitrile and then in dichloroethane 5.4 g are retained.

By thin-layer chromatography with a methylene chloride/methanol mixture (95/5) as an eluent two faint side-spots are obtained.

Intermediate product 3.1

5-[β-(β'-methoxyethoxy)-ethoxy]-3-amino-2-N-laurylcarbonamido-indole

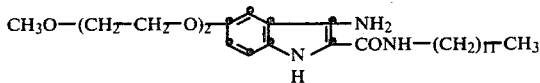

29.3 g of 5-[β-(β'-methoxyethoxy)-ethoxy]-3-(4-methoxyphenylazo)-2-N-laurylcarbonamido-indole, dissolved in 500 ml of anhydrous ethanol, are reduced with Raney nickel as a catalyst under $10^4$ kPa of hydrogen pressure. After the catalyst has been filtered off the filtrate is poured into water of 50° C. The precipitate formed is filtered with suction and recrystallized from methanol.

Yield: 17 g. Melting point: 100° C.

By thin-layer chromatography with a methylene chloride/methanol mixture (95/5) as an eluent two very faint side-spots are detected.

Intermediate product 3.2

5-[β-(β'-methoxyethoxy)-ethoxy]-3-(4-methoxyphenylazo)-2-N-laurylcarbonamido-indole

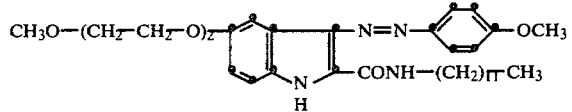

13.5 g of p-anisidine, dissolved in 33 ml of water and 33 ml of strong hydrochloric acid, are diazotized at 5° C. with a solution of 8.7 g of sodium nitrite in 33 ml of water. After stirring for 30 min the excess nitrite is destroyed with urea. The diazonium solution is added at 5° C. to a solution of 42 g of 5-[β-(β'-methoxyethoxy]-2-N-laurylcarbonamido-indole and 26.6 g of potassium hydroxide in 535 ml of ethylene glycol monomethyl ether. By adding 700 ml of water and 133 ml of strong hydrochloric acid a precipitate forms, which is filtered with suction, washed with sodium acetate solution and water, dried and recrystallized from methanol.

Yield: 38 g. Melting point: 109° C.

By thin-layer chromatography with a methylene chloride/methanol mixture (95/5) as an eluent no sidespots are detected.

Intermediate product 3.3

5-[β-(β'-methoxyethoxy)-ethoxy]-2-N-laurylcarbonamido-indole

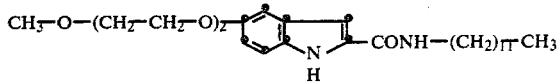

61.4 g of 2-carbethoxy-5-[β-(β'-methoxyethoxy)-ethoxy]-indole (intermediate product 1.8) and 55.5 g of laurylamine are melted together in an oil-bath at 170° C. under reduced pressure for 16 h and then cooled. Thereupon 200 ml of benzine are added and the mixture is cooled in ice with stirring. The precipitate formed is filtered with suction, washed with benzine and dried.

Yield: 42 g. Melting point: 74° C.

By thin-layer chromatography with a methylene chloride/methanol mixture (98/2) as an eluent three faint side-spots are detected.

Colour-providing compound 4

10.4 g of 5-[β-(β'-methoxyethoxy)-ethoxy]-3-amino-2-N-(γ-lauryloxypropyl)-carbonamido-indole are dissolved at 50° C. in 190 ml of ethylene glycol monomethyl ether. To this solution 9.4 g of 5-hydroxy-8-(2-methylsulphonyl-4-nitrophenylazo)-2-naphthaline sulphonylchloride (prepared according to the Belgian Patent Specification No. 796,041 already mentioned hereinbefore, page 26) and a solution of 5 ml of triethylamine in 10 ml of ethylene glycol monomethyl ether are added gradually and simultaneously. The mixture is stirred for 30 min, whereupon 100 ml of water are added and the whole is acidified with 5 ml of hydrochloric acid. The precipitate formed is filtered with suction, washed with dilute methanol and dried.

Yield: 19 g.

The product is purified by grinding under acetonitrile and by dissolving at 60° C. in ethylene glycol monomethyl ether, filtration and precipitation. Finally it is again stirred under acetonitrile at 60° C. and dried.

Yield: 7.4 g.

By thin-layer chromatography with a methylene chloride/methanol mixture (95/5) as an eluent still some very faint side-spots are detected.

Colour-providing compound 5

10.4 g of 5-[β-(β'-methoxyethoxy)-ethoxy]-3-amino-2-N-(γ-lauryloxypropyl)-carbonamido-indole are dissolved at 50° C. in 190 ml of ethylene glycol monomethyl ether. To this solution 8.9 g of 1-phenyl-3-methyl-4-(2-methoxy-5-chlorosulphonylphenylazo)-pyrazolone-(5) and a solution of 5 ml of triethylamine in 10 ml of ethylene glycol monomethyl ether are added gradually and simultaneously. The mixture is stirred at 60° C. for 1 h. The precipitate formed is filtered with suction, first washed with ethylene glycol monomethyl ether and then with methanol, and dried.

Yield: 9.5 g.

The precipitate being still hot is dissolved in 400 ml of methylene chloride and is precipitated again by the addition of 200 ml of n-hexane. This precipitate is filtered with suction, successively washed with methylene chloride and then with n-hexane, and dried.

Yield: 7 g.

By thin-layer chromatography with a methylene chloride/methanol mixture (95/5) as an eluent only one faint side-spot is detected.

Intermediate product 5.1

1-phenyl-3-methyl-4-(2-methoxy-5-chlorosulphonyl-phenylazo)-pyrazolone-(5)

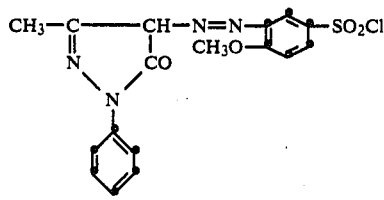

826 g of the sodium salt of 1-phenyl-3-methyl-4-(2-methoxy-5-sulphonic acid phenylazo)-pyrazolone-(5) are stirred in 6 l of toluene, whereupon as much of a mixture of toluene and water is distilled that the condensate is clear. Then fresh toluene is added so as to restore the original volume, whereupon the solution is allowed to cool to 70° C. Then 80 ml of dimethylformamide are added and thereafter 580 ml of thionyl chloride are added at 70° C. in 30 min. The mixture is stirred at 80° C. for another 30 min and the end of the reaction is established by thin-layer chromatography. The excess thionyl chloride is evaporated at 90° C. whereupon the reaction is finished under slightly reduced pressure. The reaction mixture is allowed to cool to 25° C. and the precipitate formed is filtered with suction and washed with 1 l of toluene. It is dried first at 30° C. in a ventilated oven and then in a vacuum oven.

Yield: 882 g.

Every mole of the product contains 1 mole of sodium chloride.

By thin-layer chromatography with methylene chloride/methanol mixture (98/2) as an eluent a faint side-spot of dye sulphonic acid is detected.

Intermediate product 5.2

Sodium salt of 1015 g of 3-amino-4-methoxybenzenesulphonic acid are stirred in 5 l of ice-water and 1 l of strong hydrochloric acid. To this mixture a solution of 352 g of sodium nitrite in 2 l of water is dropwise added at 0°–5° C. A mixture of 10 l of water, 1272 g of sodium carbonate (an excess for counteracting the formation of foam) and 915 g of 1-phenyl-3-methylpyrazolone-(5) is stirred and cooled externally with ice. To this solution the above diazonium solution is gradually added at 0°–15° C. and the whole is stirred for ½ h. The precipitate formed is filtered with suction and washed with 5% aqueous sodium chloride solution. Then it is dried, first in a ventilated drying oven at 30° C. and then in a vacuum drying oven.

Yield: 2225 g of product, which still contains some water as well as 7% of sodium chloride.

By thin-layer chromatography with a methylene chloride/methanol mixture (80/20) as an eluent no side-spots are detected.

Colour-providing compound 6

9.25 g of 5-(β-hydroxyethoxy)-3-amino-2-N-(γ-lauryloxypropyl)-carbonamido-indole are dissolved at 40° C. in 200 ml of ethylene glycol monomethyl ether. First 6.7 g of sodium hydrogen carbonate are added at once and then 16.5 g of 5-methylsulphonamido-4-(p-chlorosulphonylphenylazo)-1-hydroxy-2-N-butylnaphthaline sulphonamide (intermediate product 1.1) are added portionwise. The product desired is precipitated by the addition of 300 ml of water, filtered with suction, washed with dilute ethanol, dissolved at 40° C. in a solution of 100 ml of ethylene glycol monomethyl ether and 0.5 g of ascorbic acid, precipitated again with 180 ml of water, filtered with suction, washed with dilute methanol and dried.

Yield: 17.4 g.

By thin-layer chromatography with a methylene chloride/methanol mixture (80/20) as an eluent only a very faint side-spot is detected.

Intermediate product 6.1

5-(β-hydroxyethoxy)-3-amino-2-N-(γ-lauryloxy-propyl)-carbonamido-indole

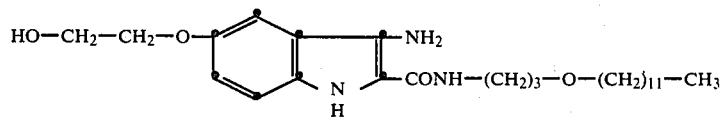

1-phenyl-3-methyl-4-(2-methoxy-5-sulphonic acid phenylazo)-pyrazolone-(5)

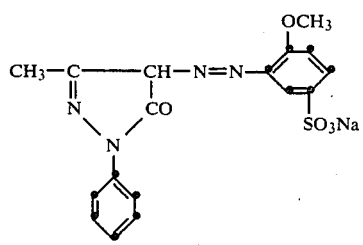

42 g of 5-(β-hydroxyethoxy)-3-(4-methoxyphenylazo)-2-N-(γ-lauryloxypropyl)-carbonamido-indole are reduced at 75° C. in ethyl acetate with Raney nickel as a catalyst under $10^4$ kPa pressure of hydrogen. Then the catalyst is filtered off and the filtrate is mixed with 500 ml of benzine. The precipitate formed is filtered with suction and washed with benzine.

Yield: 27.5 g.

By thin-layer chromatography with a methylene chloride/methanol mixture (95/5) as an eluent only two very faint side-spots are obtained.

Intermediate product 6.2

5-(β-hydroxyethoxy)-3-(4-methoxyphenylazo)-2-N-(γ-lauryloxypropyl)-carbonamido-indole

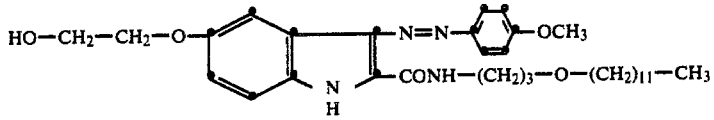

19 g of p-anisidine are diazotized in 45 g of ice and 45 ml of strong hydrochloric acid with a solution of 11.5 g of sodium nitrite in 25 ml of water. Then a solution is prepared of 37.5 g of 5-(β-hydroxyethoxy)-2-N-(γ-lauryloxypropyl)-carbonamido-indole in 400 ml of ethylene glycol monomethyl ether and 200 ml of dimethylformamide together with 15 g of potassium hydroxide. To this solution the above prepared diazonium solution is added dropwise at 5° C. with stirring. The whole is stirred for another ½ h and acidified with hydrochloric acid. The precipitate formed is filtered with suction, washed with methanol, dried and recrystallized from 300 ml of ethanol.

Yield: 36 g. Melting point: 119° C.

Intermediate product 6.3

5-(β-hydroxyethoxy)-2-N-(γ-lauryloxypropyl)-carbonamido-indole

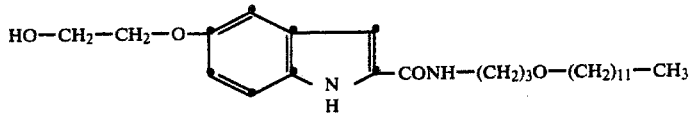

7.5 g of 2-carbethoxy-5-(β-hydroxyethoxy)-indole and 11 g of γ-lauryloxypropylamine are heated under reduced pressure in an oil-bath at 170° C. for 15 h. The obtained 5-(β-hydroxyethoxy)-2-N-(γ-lauryloxypropyl)-carbonamido-indole is purified chromatographically.

Yield: 4 g. Melting point: 99° C.

By thin-layer chromatography with a methylene chloride/methanol mixture (98/2) as an eluent no side-spots are detected.

Intermediate product 6.4

2-(carbethoxy-5-(β-hydroxyethoxy)-indole

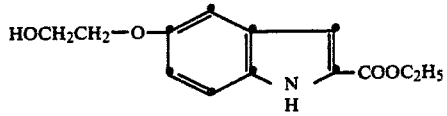

50 g of 2-methyl-2-[4-(β-hydroxyethyl)-phenylazo]-acetylacetic acid ethyl ester are dropwise added with stirring and refluxing to 120 ml of 3 N solution of hydrochloric acid in ethanol and stirred with refluxing for still 1 h. The mixture is poured with stirring into water, whereupon the supernatant water is decanted. The reaction mixture is dissolved in ethanol and poured into water, whereupon the precipitate formed is filtered with suction.

Yield: 24 g. Melting point: 158° C.

By thin-layer chromatography with a methylene chloride/methanol mixture (95/5) as an eluent two very faint side-spots are detected.

Intermediate product 6.5

2-methyl-2-[4-(β-hydroxyethoxy)-phenylazo]-acetylacetic acid ethyl ester

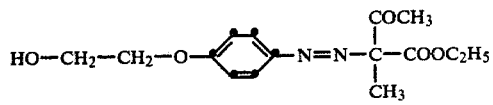

65.4 g of 4-(β-hydroxyethoxy)-aniline, mixed with 70 ml of strong hydrochloric acid and 78 g of ice, are diazotized with stirring at 0° C. with a solution of 22.1 g of sodium nitrite in 50 ml of water. The reaction mixture is stirred for 1 h, whereupon 33 g of sodium acetate are added. The obtained diazonium solution is then added to a mixture made of a solution of 47.5 g of α-methylacetylacetic acid ethyl ester in 300 ml of methanol, 300 g of ice and a solution of 21.8 g of potassium hydroxide in 30 ml of water. The whole is stirred at about 5° C. for 4 h and extracted with toluene. The extract is washed with water, dried and evaporated in a rotary evaporator. The residual 65 g of oil are directly further transformed without purification.

Colour-providing compound 7

7.1 g of 5-(β-methoxyethoxy)-3-amino-2-N-(γ-lauryloxypropyl)-carbonamido-indole are stirred with 1 g of ascorbic acid in 150 ml of ethylene glycol monomethyl ether at 40° C., whereupon 5 g of sodium hydrogen carbonate are added with stirring. Then 10.6 g of 5-methylsulphonamido-4-(p-chlorosulphonyl-phenylazo)-1-hydroxy-2-N-butylnaphthalinesulphonamide (intermediate product 1.1) are added portionwise. The reaction product is precipitated by adding 50 ml of water, filtered with suction, mixed with stirring with 250 ml of dilute methanol, filtered with suction and dissolved at 60° C. in 100 ml of ethylene glycol monomethyl ether, which contains 0.5 g of ascorbic acid. The desired product is precipitated again by the addition of 60 ml of water and filtered with suction once again. It is washed with dilute methanol and dried.

Yield: 10.1 g.

By thin-layer chromatography with a mixture of methylene chloride and methanol (80/20) as an eluent only two vert faint side-spots are detected.

Intermediate product 7.1

5-(β-methoxyethoxy)-3-amino-2-[N-(γ-lauryloxypropyl)-carbonamido]-indole

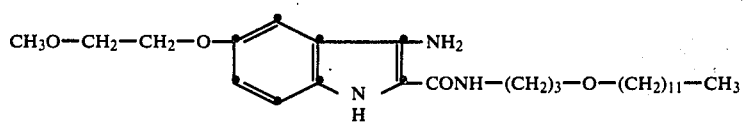

13 g of 5-(β-methoxyethoxy)-3-(4-methoxyphenylazo)-2-[N-(γ-lauryloxypropyl)-carbonamido]-indole in 150 ml of ethyl acetate are reduced with Raney nickel as a catalyst at 70° C. under $10^4$ kPa of hydrogen pressure. After filtering off of the catalyst the product is precipitated with 200 ml of benzine, filtered with suction and washed with benzine.

Yield: 7.1 g. Melting point: 100.5° C.

By thin-layer chromatography with a methylene chloride/methanol mixture (95/5) as an eluent no side-spots are detected.

Intermediate product 7.2

5-(β-methoxyethoxy)-3-(4-methoxyphenylazo)-2-[N-(γ-lauryloxypropyl)-carbonamido]-indole

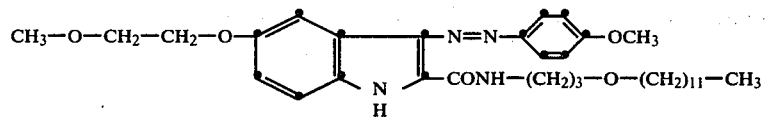

27 g of p-anisidine in a mixture of 66 ml of strong hydrochloric acid and 60 g of ice are diazotized at 5° C. with a solution of 16.6 g of sodium nitrite in 35 ml of water. The crude carbonamido-indole (intermediate product 7.3) is dissolved in 500 ml of ethylene glycol monomethyl ether. First 30 g of potassium hydroxide are added and then the diazonium solution is dropwise added at 5° C. The precipitate formed is filtered with suction, washed with methanol, stirred in water, filtered with suction, washed with methanol and dried.

Yield: 13.3 g. Melting point: 90° C.

By thin-layer chromatography no impurity is detected.

Intermediate product 7.3

5-(β-methoxyethoxy)-2-[N-(γ-lauryloxypropyl)-carbonamido]-indole

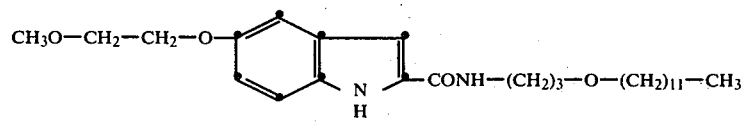

52.2 g of 2-carbethoxy-5-(β-methoxyethoxy)-indole and 73 g of γ-lauryloxypropylamine are stirred in 250 ml of toluene. As much toluene is distilled until any water still present is removed. Then a solution of 1 g of sodium in 25 ml of methanol is added at 100° C. The toluene is distilled in about 4 h until the temperature of the reaction medium has reached 140° C. The last volatile components are distilled under slightly reduced pressure. The residue is transformed without any further purification.

By thin-layer chromatography with a methylene chloride/methanol mixture (95/5) as an eluent only a faint side-spot of the starting ester is detected.

Intermediate product 7.4

2-carbethoxy-5-(β-methoxyethoxy)-indole

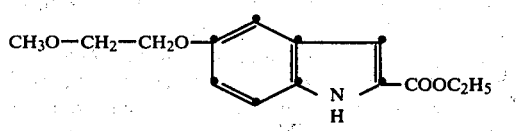

40 g of 2-methyl-2-[4-(β-methoxyethoxy)-phenylazo]-acetylacetic acid ethyl ester are added dropwise with stirring and refluxing to 100 ml of 3 N solution of hydrochloric acid in ethanol. After 1 h the reaction mixture is cooled and poured into ice-water. The precipitate formed is filtered with suction, washed with water and dried.

Yield: 27.5 g. Melting point: 74° C.

The precipitate is then recrystallized from n-hexane whereby its melting point rises to 86° C.

Intermediate product 7.5

2-methyl-2-[4-(β-methoxyethoxy)-phenylazo]-acetylacetic acid ethyl ester

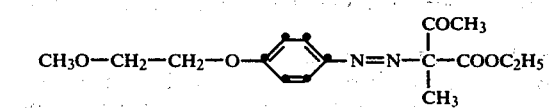

50 g of 4-(β-methoxyethoxy)-aniline in 76.5 ml of strong hydrochloric acid and 50 ml of water are diazotized at 0° C. by the dropwise addition of a solution of 22.8 g of sodium nitrite in 70 ml of water. The reaction mixture is stirred for 1 h whereupon 32 g of sodium acetate are added. Then a solution of 47.5 g of α-methylacetylacetic acid ethyl ester in 300 ml of ethanol is prepared, to which a solution of 21.6 g of potassium hydroxide in 30 ml of water is added dropwise at 0° C. Then successively 300 g of ice and the diazonium solution are added, whereupon the mixture is stirred for another 4 h. The mixture is shaken out with toluene, whereupon the toluene is evaporated. Yield: 77.5 g of a reddish brown oil, which is transformed without any further purification.

Colour-providing compound 8

11.2 g of 5-[β-(β'-butoxyethoxy)-ethoxy]-3-amino-2-[N-(γ-lauryloxypropyl)-carbonamido]-indole are dissolved at 40° C. together with 1 g of ascorbic acid in 200 ml of ethylene glycol monomethyl ether, whereupon first 6.7 g of sodium hydrogen carbonate are added at once and then 15.5 g of 5-methylsulphonamido-4-(p-chlorosulphonylphenylazo)-1-hydroxy-2-N-butylnaphthalinesulphonamide (intermediate product 1.1) are added portionwise. The mixture is diluted with 100 ml of water, whereupon the precipitate formed is filtered with suction and washed with 200 ml of dilute methanol. The precipitate is purified by dissolving it together with 0.5 g of ascorbic acid in 100 ml of ethylene glycol monomethyl ether at 60° C., precipitating with 75 ml of water, filtering with suction and washing with dilute methanol.

Yield: 17.8 g.

By thin-layer chromatography with a methylene chloride/methanol mixture (80/20) as an eluent three very faint side-spots are detected.

Intermediate product 8.1

5-[β-(β'-butoxyethoxy)-ethoxy]-3-amino-2-[N-(γ-lauryloxypropyl)-carbonamido]-indole

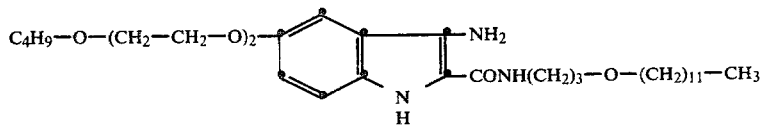

54.4 g of 5-[β-(β'-butoxyethoxy)-ethoxy]-3-(4-methoxyphenylazo)-2-[N-(γ-lauryloxypropyl)-carbonamido]-indole in 240 ml of ethyl acetate are reduced at 70° C. under 10⁴ kPa pressure of hydrogen with Raney nickel as a catalyst. After filtering off of the catalyst the reaction product is precipitated with 500 ml of benzine, filtered with suction and washed with benzine.

Yield: 35.1 g. Melting point: 77° C.

By thin-layer chromatography with a methylene chloride/methanol mixture (95/5) as an eluent still two side-spots are detected. The product is transformed without any further purification.

Intermediate product 8.2

5-[β-(β'-butoxyethoxy)-ethoxy]-3-(4-methoxyphenylazo)-2-[N-(γ-lauryloxypropyl)-carbonamido]-indole

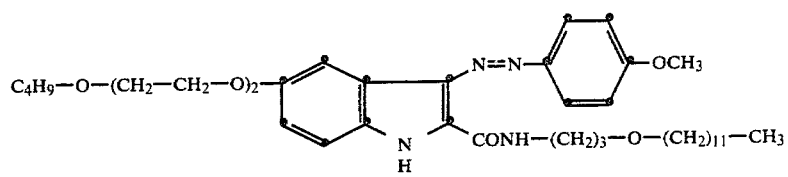

41 g of p-anisidine in 100 g of ice and 100 ml of strong hydrochloric acid are diazotized at 0° C. with a solution of 25 g of sodium nitrite in 50 ml of water. The crude indole (intermediate product 8.3) is dissolved in 600 ml of ethylene glycol monomethyl ether and mixed with 33 g of potassium hydroxide. The diazonium solution is dropwise added to this mixture at 5° C. The precipitate formed is filtered with suction, washed with methanol, stirred in water, filtered with suction, washed with methanol and recrystallized from 600 ml of methanol.

Yield: 54.7 g. Melting point: 90° C.

By thin-layer chromatography with a methylene chloride/methanol mixture (95/5) as an eluent four very faint side-spots are detected. Titration with sodium methylate in dimethylformamide: 1.49 meq/g. Calculated value: 1.47 meq/g.

Intermediate product 8.3

5-[β-(β'-butoxyethoxy)-ethoxy]-2-[N-(γ-lauryloxypropyl)-carbonamido]-indole

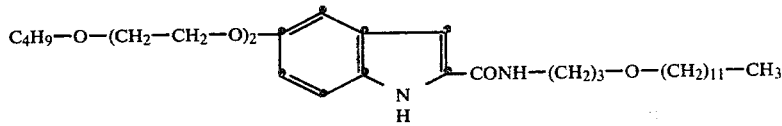

104.7 g of 2-carbethoxy-5-[β-(β'-butoxyethoxy)-ethoxy]-indole and 110 g of γ-lauryloxypropylamine are stirred in 370 ml of toluene. The toluene is distilled until the distillate is clear. A solution of 1.5 g of sodium in 50 ml of methanol is added at 100° C. The toluene is distilled within about 4 h until the temperature of the reaction mixture has reached 140° C. The last volatile components are distilled under reduced pressure. The residue is used in the following step without any further purification.

Intermediate product 8.4

2-carbethoxy-5-[β-(β'-butoxyethoxy)-ethoxy]-indole

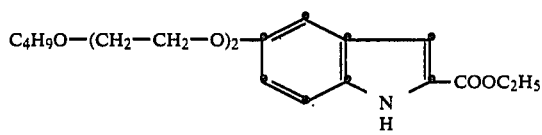

94.8 g of 2-methyl-2-{4-[β-(β'-butoxyethoxy)-ethoxy]-phenylazo}-acetylacetic acid ethyl ester are added dropwise to 200 ml of 3 N alcoholic hydrochloric acid solution. After 1 h of reflux the reaction mixture is poured into water and extracted with methylene chloride. The extract is washed with water, dried and evaporated.

Yield: 79 g of an oil, which is further transformed as such.

Intermediate product 8.5

2-methyl-2-{4-[β-(β'-butoxyethoxy)-ethoxy]-phenylazo}acetyl-acetic acid ethyl ester

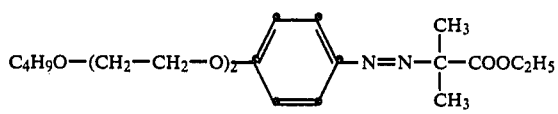

88.8 g of 4-[β-(β'-butoxyethoxy)-ethoxy]-aniline in 91.8 ml of strong hydrochloric acid and 60 ml of ice are diazotized at 0° C. with a solution of 27.3 g of sodium nitrite in 84 ml of water. After 1 h of stirring 38.4 g of sodium acetate are added. This diazonium solution is added to a mixture of 57 g of α-methylacetylacetic acid ethyl ester, 360 ml of ethanol, a solution of 25.8 g of potassium hydroxide in 36 ml of water and 360 g of ice. After allowing to stand overnight in the refrigerator the reaction mixture is shaken out with toluene. The solution in toluene is washed with water, dried and evaporated.

Yield: 130 g of oil, which is further transformed as such.

By thin-layer chromatography with a methylene chloride/methanol mixture (98/2) as an eluent still three side-spots are detected.

The colour-providing compounds according to the present invention are incorporated into the coating compositions of the layers of the photographic material according to one of the usual methods. The amount of colour-providing compound used per liter of coating composition varies within relatively wide limits, the most favourable concentration being found out by means of simple tests. For example per liter of coating composition 5 to 80 g, preferably 20 to 40 g of colour-providing compound are used. The necessary association between non-migratory colour-providing compound and silver halide for obtaining the desired effect can be realized, e.g., by incorporating the non-migratory compounds from alkaline solutions into the coating compositions and by taking advantage of the water-solubilizing groups present. However, the non-migratory colour-providing compounds can also be incorporated into the layers according to one of the known emulsifying processes. Suchlike processes are described, e.g., in the UK Patent Specifications Nos. 791,219 filed Nov. 9, 1955 by Kodak Ltd. and 1,099,414 to 1,099,417 all filed Jan. 25, 1965 by Gevaert Agfa N.V. Further it is possible to prepare aqueous dispersions of the colour-providing compounds and to add them to the respective coating compositions. For this purpose aqueous suspensions of the colour-providing compound are finely ground, e.g. by intensive stirring after the addition of sharp-edged sand or by applying ultrasonic waves. In another embodiment it may be desirable, e.g., to incorporate the colour-providing compounds together with siliver halide and optionally with developing substances in the form of so-called microcapsules into the layer. In that case also two or more differently sensitized light-sensitive silver halide emulsions and the corresponding non-migratory compounds can be united in one layer like the so-called mixed emulsions as has been described, e.g., in the U.S. Pat. No. 2,698,794 of Leopold Godowsky, issued Jan. 4, 1955. The non-migratory colour-providing compounds may be incorporated into a light-sensitive layer itself or into an adjacent layer. For example a compound splitting off a cyan dye is associated with the red-sensitive layer, a compound splitting off a magenta dye is associated with the green-sensitive layer, and a compound splitting off a yellow dye is associated with the blue-sensitive layer.

By "association" and "associated" is understood that the mutual arrangement of silver halide emulsion layers and of colour-providing compounds is of such nature that an interaction is possible between them, which allows an image-wise correspondence between the silver image formed and the image-wise distribution of the released diffusing dye.

Appropriately the associated colour-providing compound is incorporated into the silver halide emulsion layer itself or into a layer adjacent to it, wherein this adjacent layer preferably lays behind the silver halide emulsion layer (seen in the direction of the incident light upon exposure). The colour-providing compounds according to the invention are image-wise oxidized by oxidation products of developing agents during the development of the silver image. As a result of the influence of the developer alkali or the activator alkali they are subjected to a cleavage reaction in which the dye residues are released in the form of diffusing dye sulphonamides. For development the usual photographic developing agents are suited as far as they are capable of oxidizing in oxidized form the colour-providing compounds according to the invention. Examples of suitable developing agents are:

hydroquinone,
N-methylaminophenol,
1-phenyl-3-pyrazolidinone,
1-phenyl-4,4-dimethyl-3-pyrazolidinone,
1-phenyl-4-methyl-4-hydroxymethyl-3-pyrazolidinone,
1-phenyl-4,4-bishydroxymethyl-3-pyrazolidinone, aminophenols,
N,N-diethyl-p-phenylenediamine,
N-ethyl-N-hydroxyethyl-p-phenylenediamine,
3-methyl-N,N-diethyl-p-phenylenediamine and
N,N,N',N'-tetra-alkyl-p-phenylenediamines, such as tetramethyl-p-phenylenediamine, triethylsulphobutyl-p-phenylenediamine, 1,4-bis-pyrrolidinobenzene, and
reductones.

Special attention has to be drawn to the fact that the choice of developing agents in the process according to the present invention is not limited to colour developing agents. The usual black-and-white developing agents can be used too, which is to be considered as an advantage because of the weaker tendency of the latter to discolour.

The developing substances can already be present in the layers of the photographic colour material where they are activated by the alkaline activator liquid, or in the alkaline processing liquid or paste. In particular cases the use of auxiliary developing compounds can be dispensed with viz. when the colour-forming compounds of the present invention have developing properties by themselves. In such a case the colour-forming compound is immediately oxidized by developable silver halide.

As the image-wise distribution of the diffusing dye, which has been released during development, corresponds with the developed silver image, direct-positive silver halide emulsions should be used for making positive transfer colour images. If usual negative emulsions are used a suitable reversal process has to be applied.

Such a reversal process is at disposal in the silver complex diffusion transfer process. The photographic reversal by the use of the silver complex diffusion transfer process for the production of positive colour images by making use of conventional colour couplers is described, e.g., in the U.S. Pat. No. 2,763,800 of Bruce A. Curley, issued Sept. 18, 1956. By replacing the colour couplers by the mentioned colour-providing compounds a light-sensitive element is realized that is suited for the dye diffusion transfer process. Such a light-sensitive element comprises, e.g., at least one combination of a light-sensitive silver halide emulsion layer and a binder layer associated therewith, which contains developing nuclei for the physical development as well as a colour-providing compound.

Upon development the exposed part of the silver halide is chemically developed in the light-sensitive silver halide emulsion layer, whereas the non-exposed part is transferred by means of a silver halide solvent into the associated binder layer containing developing nuclei and physically developed therein. When for the physical development a developing substance is used, which in its oxidized form as a result of a reaction with a colour-providing compound incorporated in said layer is capable of releasing a diffusing dye, then an image-wise distribution of diffusing dyes is realized. These dyes can be transferred to an image-receiving layer and produce a positive colour image therein.

For the reversal with the use of compounds that image-wise split off development-inhibiting agents, the light-sensitive element consists of at least one layer combination of a light-sensitive silver halide emulsion layer and a second emulsion layer that contains the colour-providing compound and is developable without exposure. The light-sensitive silver halide emulsion layer is developed, e.g. with colour developing agents, in the presence of certain compounds that split off development-inhibiting substances upon reacting with the oxidized colour-developing agent. The development-inhibiting substances released image-wise in the light-sensitive layer diffuse in the adjacent emulsion layer, which is developable without exposure, and there image-wise inhibit the development. Thereby the non-inhibited (positive) parts of the emulsion layer that is developable without exposure are developed by the residual developing agent, whose oxidation products then react with the non-diffusing colour-providing compounds according to the invention and release diffusing dyes, which are transferred image-wise to the image-receiving element. Suitable compounds that split off development-inhibiting substances upon reacting with oxidation products of colour-developing agents are, e.g., the known DIR-couplers (Development Inhibitor Releasing), which are colour couplers containing in the coupling position an inhibitor rest that can be split off. Suchlike DIR-couplers are described, e.g., in the U.S. Pat. No. 3,227,554 of Charles R. Barr, John Williams and Keith E. Whitmore, issued Jan. 4, 1966.

Another group of compounds that split off development inhibitors upon reacting with oxidation products of colour developing agents is described in the U.S. Pat. No. 3,632,345 of Paul Marx, Ulrich Heb, Rigobert Otto, Walter Puschel and Willibald Pelz, issued Jan. 4, 1972. They are not colour couplers. Correspondingly, no dyes are formed during the release of development inhibitors. According to the German Patent Specification No. 1,229,389 filed Mar. 28, 1964 by Kodak Ltd., also suitably substituted, non-diffusing hydroquinone compounds can be used in such a process, which upon reacting with oxidation products of developing agents are oxidized to the corresponding quinones and split off development-inhibiting mercaptanes.

In principle all the direct-positive silver halide emulsions are suited that produce a positive silver image and a corresponding image-wise distribution of developing agent oxidation products during a simple development. For example those silver halide emulsions are considered wherein by exposure or by a chemical treatment a developable fog has been produced, which is destroyed image-wise during the image-wise exposure when certain conditions are fulfilled. In the unexposed areas the fog is maintained so that during the subsequent development a direct-positive silver image is obtained and in correspondence therewith an image-wise distribution of diffusing dye, when a colour-providing compound according to the invention is associated with the direct-positive silver halide emulsion.

Another group of direct-positive silver halide emulsions that may be used in dye image formation according to the present invention comprises the so-called unfogged direct-positive silver halide emulsions whose silver halide grains are light-sensitive mainly in the core. A latent image forms mainly in the core of the silver halide grains during the image-wise exposure of these emulsions.

The development of suchlike unfogged direct-positive silver halide emulsions, however, is carried out under fogging conditions, wherein fog is produced mainly in the unexposed areas and a positive image is developed during development. The unfogged direct-positive silver halide emulsions are characterized thereby that exposed samples preferably produce no silver image or at most produce a silver image with very low density when they are developed in a typical surface developer of the following composition:

| | |
|---|---|
| p-hydroxyphenylglycine | 10 g |
| sodium carbonate-1-water | 100 g |
| water to make | 1000 ml, | whereas a silver image of sufficient density forms when said exposed samples are developed in an internal-type developer of the following composition:

| | |
|---|---|
| hydroquinone | 15 g |

| | |
|---|---|
| monomethyl-p-aminophenol sulphate | 15 g |
| anhydrous sodium sulphite | 50 g |
| potassium bromide | 10 g |
| sodium hydroxide | 25 g |
| sodium thiosulphate-5-water | 20 g |
| water to make | 1000 ml. |

The selective fogging of the image-wise exposed unfogged direct-positive emulsions can be performed before or during the development by treating them with a fogging agent. Suitable fogging agents are reducing agents such as hydrazine or substituted hydrazines. Reference is made, e.g., to the U.S. Pat. No. 3,227,552 of Keith E. Whitmore, issued Jan. 4, 1966. Examples of unfogged direct-positive emulsions are those wherein the cores of the silver halide grains show crystal defects (U.S. Pat. No. 2,592,250 of Edward Philip Davey and Edward Bowes Knott, issued Apr. 8, 1952) or those with covered grain structure (published German Patent Application No. 2,308,239 filed Feb. 20, 1973 by AgfaGevaert AG).

The emulsions can also be chemically sensitized, e.g. by adding sulphur-containing compounds, e.g. allyl isothiocyanate, allyl thiourea, sodium thiosulphate and the like, during the chemical ripening stage. Also reducing agents, e.g. the tin compounds described in the Belgian Patent Specifications Nos. 493,464 filed Jan. 24, 1950 and 568,687 filed June 18, 1958, both by Gevaert Photo-Producten N.V., and polyamines such as diethylenetriamine or derivatives of aminomethanesulphonic acid, e.g. according to the Belgian Patent Specification No. 547,323 filed Apr. 26, 1956 by Gevaert Photo-Producten N.V., can be used as chemical sensitizers. Other suitable chemical sensitizers are noble metals and noble metal compounds such as gold, platinum, palladium, iridium, ruthenium and rhodium. This method of chemical sensitization has been described in the article of R. KOSLOWSKY, Z.Wiss.Photogr.Photophys.-Photochem. 46, 65–72 (1951).

Further it is possible to sensitize the emulsions with polyalkylene oxide derivatives, e.g. with polyethylene oxide having a molecular weight between 1000 and 20,000, or with condensation products of alkylene oxides and aliphatic alcohols, glycols, cyclic dehydration products of hexitols, alkyl-substituted phenols, aliphatic carboxylic acids, aliphatic amines, aliphatic diamines and amides. The condensation products have a molecular weight of at least 700, preferably of more than 1000. For obtaining special effects these sensitizers of course can be combined with each other as described in Belgian Patent Specification No. 537,278 filed Apr. 12, 1955 and U.K. Patent Specification No. 727,982 filed Feb. 5, 1952, both by Gevaert Photo-Producten N.V.

The emulsions can also be spectrally sensitized, e.g. by the usual mono- or polymethine dyes such as acidic or basic cyanines, hemicyanines, oxonols, hemioxonols, styryl dyes or others, also tri- or polynuclear methine dyes, e.g. rhodacyanines or neocyanines. Such sensitizers are described, e.g., by F. M. HAMER in "The Cyanine Dyes and Related Compounds" (1964) Interscience Publishers, John Wiley & Sons, New York.

The emulsions may contain the usual stabilizers such as, e.g., homopolar or salt-like compounds of mercury with aromatic or heterocyclic rings such as mercaptotriazoles, simple mercury salts, sulphonium mercury double salts and other mercury compounds. Other suitable stabilizers are azaindenes, preferably tetra- or penta-azaindenes, especially those substituted with hydroxyl or amino groups. Compounds of this kind are described by BIRR in Z.Wiss.Photogr.Photophys.-Photochem. 47, 2–27 (1952). Still other suitable sensitizers are among others heterocyclic mercapto compounds, e.g. phenylmercaptotetrazole, quaternary benzothiazole derivatives, benzotriazole and the like.

As binding agent for the photographic layers preferably gelatin is used. However, it can be replaced wholly or partially by other natural or synthetic binding agents. Examples of natural binding agents are alginic acid and its derivatives such as salts, esters and amides, cellulose derivatives such as carboxymethylcellulose, alkylcellulose such as hydroxyethylcellulose, starch and its derivatives such as ethers or esters, or carragenates. Examples of synthetic binding agents are polyvinyl alcohol, partially saponified polyvinyl acetate, polyvinylpyrrolidone and the like.

Hardening of the layers can occur in the usual way, e.g. with formaldehyde or halogenated aldehydes containing a carboxyl group such as mucobromic acid, diketones, methanesulphonic acid esters, dialdehydes.

For carrying out the dye diffusion transfer process according to the present invention preferably a two-sheet system is used, which consists of a light-sensitive element containing one or more silver halide emulsion layers and the non-migratory colour-providing compounds associated therewith and of a separate image-receiving element wherein the desired colour image is produced by the imagewise transferred diffusing dyes. For that purpose a firm contact between the light-sensitive element and the image-receiving element is necessary for a finite period of time during development. In this way the produced imagewise distribution of diffusing dyes produced in the light-sensitive element as a result of development can be transferred to the image-receiving element. The contact is made after the development has been started. For carrying out the dye diffusion transfer process also a material can be used wherein the light-sensitive element and the image-receiving element form an integral unit; it is also called a one-sheet material. A separation of the light-sensitive element from the image-receiving element after terminating the process of development, even after the dye transfer, is not necessary herein. Such an embodiment is described, e.g., in the published German Patent Application No. 2,019,430 filed Apr. 22, 1970 by Agfa-Gevaert AG.

The light-sensitive element constitutes an essential part of the photographic material of the present invention. In the case of a one-dye diffusion transfer process it contains a light-sensitive silver halide emulsion layer and a non-migratory colour-providing compound associated therewith. The non-migratory compound can be present in a layer adjacent to the silver halide emulsion layer or in the silver halide emulsion layer itself. In the latter case the colour of the image dye is preferably chosen such that the predominating absorption range of the colour-providing compound does not correspond with the predominating sensitivity range of the silver halide emulsion layer.

For the production of multicolour transfer images in natural colours, however, the light-sensitive element contains three such associations of colour-providing compound and light-sensitive silver halide emulsion layer. Normally the absorption range of the colour-providing compound essentially corresponds with the range of the spectral sensitivity of the associated silver halide emulsion layer. However, a condition for a sensitivity as high as possible is that each colour-providing combination be incorporated into a separate binder layer behind the silver halide emulsion layer (see in the direction of the incident light upon exposure).

The developing agent oxidation products produced on development of a silver halide emulsion of course should only act upon the associated colour-providing compound. Therefore, generally separating layers are present in the light-sensitive element, which effectively prevent the diffusion of the developing agent oxidation products into other non-associated layers.

For example, these separating layers may contain suitable substances that react with the developing agent oxidation products, e.g. non-migratory hydroquinone derivatives or, if the developing agent is a colour-developing agent, non-migratory colour couplers. Therefore, in a preferred embodiment the light-sensitive element has the following composition (from top to bottom):

a blue-sensitive silver halide emulsion layer, a layer with non-migratory compound releasing a diffusing yellow dye, a separation layer, a green-sensitized silver halide emulsion layer, a layer with non-migratory compound releasing a diffusing magenta dye, a separation layer, a red-sensitized silver halide emulsion layer and layer with non-migratory compound releasing a diffusing cyan dye.

Of course, the silver halide emulsion layers can be arranged in another sequence with the proviso, however, that the layers with the colour-providing systems are rearranged also so that the required association is maintained.

The image-receiving material contains an image-receiving layer that essentially comprises a binding agent as well as the dye-mordanting agent for immobilizing the diffusing dyes.

Preferred mordanting agents for acidic dyes are long-chained quaternary ammonium or phosphonium compounds or ternary sulphonium compounds, e.g. those described in the U.S. Pat. Nos. 3,271,147 of Walter M. Bush and 3,271,148 of Keith E. Whitmore, both issued Sept. 6, 1966. In addition thereto determined metal salts and their hydroxides can be used that form sparingly soluble compounds with the acidic dyes. The dye-mordanting agents are dispersed in the receiving layer in one of the usual hydrophilic binding agents, e.g. in gelatin, polyvinylpyrrolidone, partially or wholly hydrolyzed cellulose esters and the like. Of course many binding agents can also act as a mordanting agent, e.g. copolymers or polymer mixtures of vinyl alcohol and N-vinylpyrrolidone as described, e.g., in the published German Patent Specification No. 1,130,284 filed Dec. 1, 1958 by Polaroid, further polymers of nitrogen-containing quaternary bases, e.g. polymers of N-methyl-2-vinylpyridine as described, e.g., in the U.S. Pat. No. 2,484,430 of Robert H. Sprague and Leslie G. S. Brooker, issued Oct. 11, 1949. Other usable mordanting binding agents are, e.g. guanylhydrazone derivatives of acylstyrene polymers as described, e.g., in the published German Patent Application No. 2,009,498 filed Feb. 28, 1970 by Agfa-Gevaert AG. Still other usable mordanting binding agents are cationic polyurethanes with an average molecular weight between 10,000 and 60,000, which are water-soluble or dispersable and derive from a diisocyanate as has been described in the published German Patent Application No. 2,315,304 filed Mar. 27, 1973 by Agfa-Gevaert AG. Generally, however, other binding agents, e.g. gelatin, are added to the last mentioned mordanting binding agents.

The usual supports of photographic practice can be used as supports for the light-sensitive material and the receiving material, e.g. paper and films of cellulose esters, polyethylene terephthalate, polycarbonates and other film-forming polymers.

For processing the image-wise exposed photographic material, the light-sensitive element is first brought into contact with the aqueous alkaline processing solution. The image-wise exposed silver halide emulsion layers are developed in the presence of the developing compound, which already previously can be incorporated in the light-sensitive element. Thereby an image-wise distribution of oxidation products of developing compound is produced in correspondence with the silver image formed, which oxidize the associated colour-providing compound, whereupon the latter by reacting with the alkali of the activator splits off the diffusing dye and by diffusion image-wise transfers the dye to the image-receiving material when it is in contact therewith.

The aqueous alkaline processing liquid may contain additives increasing the viscosity, e.g. hydroxyethylcellulose. In addition the processing solution may contain in a known way development accelerators, stabilizers, solvents for silver halide, fogging agents, anti-oxidizing agents and still other additives.

By transfer in register of the monochrome yellow, magenta and cyan image information of a multicolour original to the same image-receiving material, a multicolour copy can be obtained, which is suited e.g. for colourproofing.

The process as well as the materials according to the invention are suited likewise for the multicolour production of technical drawings and geographic maps as well as for the production of transparencies for overhead projection. The following examples illustrate the present invention.

EXAMPLE 1

Material 1

To a subbed waterproof paper support of 110 g/m2, which has been laminated with a polyethylene layer of 15 g/m2 on either side and has been subjected to a corona-discharge treatment, the following layers are successively applied:

(1) a silver-precipitating layer containing per m2 after drying:

| | |
|---|---|
| silver sulphide nuclei | 20 mg |
| 1-phenyl-3-pyrazolidinone | 150 mg |
| magenta-providing compound nr. 1 of table 1 | 800 mg |
| gelatin | 2 g |

(2) a negative gelatin-silver chloride emulsion layer containing per m2 an amount of silver chloride equivalent with 1.1 g of silver, 2.5 g of gelatin and 2.7 g of octadecylhydroxyquinonesulphonic acid;

(3) an intermediate layer containing per m2 600 mg of octadecylhydroquinonesulphonic acid and 2 g of gelatin;

(4) a protective layer containing 2 g of gelatin per m2.

Comparison material I

It is composed as material 1 except that the dye no. 1 is replaced by the magenta-providing comparison dye no. I of table 2, which follows after the description of the examples.

Dye-image-receiving material

A layer is applied to the same support as described for the above photographic materials from the following composition per m2:

| | |
|---|---|
| gelatin | 4.5 g |
| triphenyl-n-hexadecylphosphonium bromide | 3 g. |

Processing

After exposure through a step-wedge with constant 0.1 the photographic materials 1 and I are dipped for 50 s in the processing liquid of the following composition:

| | |
|---|---|
| sodium hydroxide | 30 g |
| hydroxyethylcellulose | 3 g |
| benzyl alcohol | 10 g |
| paraformaldehyde | 1 g |
| anhydrous sodium thiosulphate | 10 g |
| potassium bromide | 2 g |
| water to make | 1 l. |

Then the thus treated materials 1 and I as well as the above described dye-image-receiving material are treated in the COPYPROOF CP 38 (tradename) diffusion transfer apparatus, which in its tray contains the same processing liquid as described above. The thus treated materials 1 and I are brought into contact with the described dye-image-receiving material for 30 s to 7 min. After this contact the maximum densities obtained are measured and the diagrams 1 and I are plotted in FIG. 1. In this figure the maximum density (D) is plotted versus the contact time (s), which is obtained with either of the materials 1 and I.

It clearly appears from these curves that material 1 attains a high density more rapidly than material I and that this density remains constant with the result that after a given minimum period of time the time of contact has practically no influence anymore on the density and hence is no longer critical.

EXAMPLE 2

Example 1 is repeated with the difference, however, that for manufacturing the materials 2 and II the magenta dye-providing compound 1 is replaced by a same amount of cyan dye-providing compound 2 of table 1 and the magenta dye-providing compound I by a same amount of cyan dye-providing compound II of table 2.

Analogously to example 1 the curves of density (D) versus contact time (s) obtained with materials 2 and II are represented for illustration.

EXAMPLE 3

Example 1 is repeated with the difference, however, that the magenta dye-providing compound 1 in the separate materials 3 and 4 is replaced by a same amount of cyan dye-providing compounds 3 and 4 of table 1, and the magenta dye-providing compound I is replaced by a same amount of cyan dye-providing compound III of table 2 for making material III.

Analogously to example 1 the curves of density (D) versus contact time (s) obtained with materials 3, 4 and III are represented.

EXAMPLE 4

Example 1 is repeated with the difference, however, that upon making the materials 5 and IV the magenta dye-forming compound 1 is replaced by a same amount of yellow dye-forming compound 5 of table 1, and that the magenta dye-forming compound I is replaced by a same amount of yellow dye-forming compound IV of table 2.

Analogously to example 1 the curves of density (D) versus contact time (s) obtained with materials 5 and IV are represented.

TABLE 2

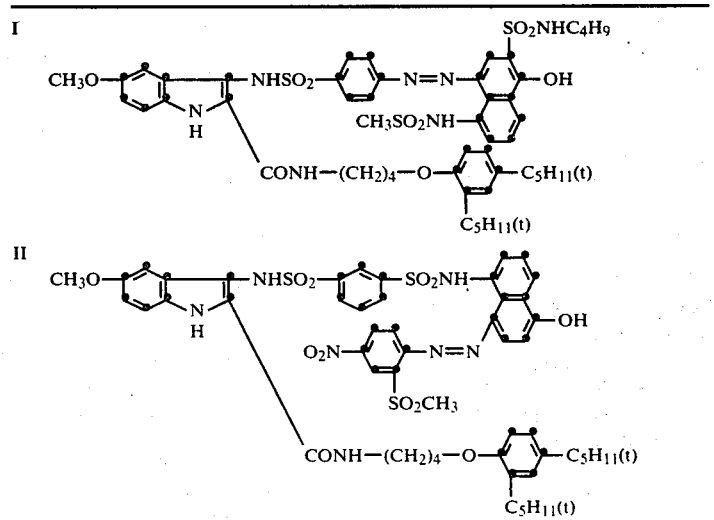

TABLE 2-continued

III 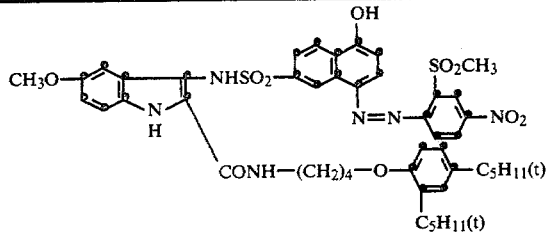

IV 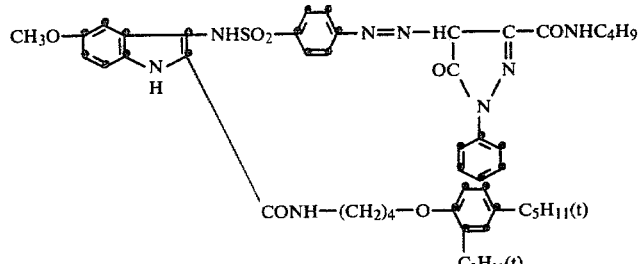

We claim:

1. Photographic diffusion transfer process for making colour images according to which a photographic material with at least one light-sensitive silver halide emulsion layer and associated with this layer a non-migratory colour-providing compound, which in its oxidized form and in alkaline medium is capable of releasing a diffusing dye, is image-wise exposed and developed with a silver halide developing agent, which in its oxidized form oxidizes the non-migratory colour-providing compound as a result of which oxidation the latter is split by a developer alkali under formation of an image-wise distribution of the released diffusing dye, characterized in that the non-migratory colour-providing compound corresponds to the following general formula:

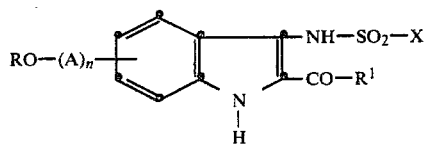

wherein:
R represents an alkyl group of 1 to 4 C atoms;
A represents an oxyalkylene group;
n is 1 or 2;
X represents a dye residue or a dye precursor, which is bound to the $SO_2$-group either directly or through Z acting as an intermediate link;
Z represents an alkylene group of 1 to 6 C atoms, an arylene group or a heterocyclic group, which is linked to the residue X either directly or by means of —O—, —S—, —$SO_2$—, —NR— (R being hydrogen or an alkyl group), —CO—, —CONH— or —$SO_2$NH—;
$R^1$ represents —$OR^2$, —$SR^2$ or

$R^2$ being hydrogen, an alkyl group with 1 to 22 C atoms, a cycloalkyl group or an aryl group, $R^3$ being one of the residues defined under $R^2$ or being an acyl residue which is derived from an aliphatic or aromatic carboxylic or sulphonic acid, and $R^4$ being hydrogen or an alkyl group with 1 to 22 C atoms.

2. Process according to claim 1, characterized in that that $R^1$ is a residue making fast to diffusion or contains such a residue and A is a —$CH_2$—$CH_2$O—group.

3. Photographic material with at least one light-sensitive silver halide emulsion layer and associated therewith a non-migratory colour-providing compound, which in its oxidized form and in an alkaline medium is capable of releasing a diffusing dye, characterized in that that the non-migratory colour-providing compound corresponds to the following general formula:

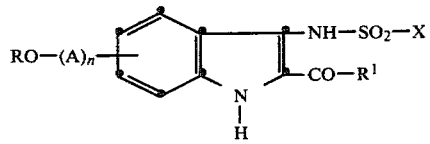

wherein:
R represents an alkyl group of 1 to 4 C atoms;
A represents an oxyalkylene group;
n is the number 1 or 2;
X represents a residue of a dye or a dye precursor, which is bound to the $SO_2$-group either directly or by means of Z acting as an intermediate link;
Z represents an alkylene group of 1 to 6 carbon atoms, an arylene group or a heterocyclic group, which is linked to the residue X either directly or by means of —O—, —S—, —$SO_2$—, —NR— (R being hydrogen or an alkyl group), —CO—, —CONH— or —$SO_2$NH—;
$R^1$ represents —$OR^2$, —$SR^2$ or

$R^2$ being hydrogen, an alkyl group with 1 to 22 C atoms, a cycloalkyl group or an aryl group, $R^3$ being one of the residues defined under $R^2$ or being an acyl residue which is derived from an aliphatic or aromatic carboxylic or sulphonic acid, and $R^4$ being hydrogen or an alkyl group with 1 to 22 C atoms.

* * * * *